(12) United States Patent
Pincus et al.

(10) Patent No.: US 8,822,419 B2
(45) Date of Patent: *Sep. 2, 2014

(54) MEMBRANE RESIDENT PEPTIDE IN ANTI-CANCER PEPTIDES CAUSES TUMOR CELL NECROSIS RATHER THAN APOPTOSIS OF CANCER CELLS

(75) Inventors: Matthew R. Pincus, Brooklyn, NY (US); Josef Michl, Little Neck, NY (US); Ehsan Sarafraz-Yazdi, New York, NY (US)

(73) Assignee: The Research Foundation of State University of New York, Albany, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/122,256

(22) PCT Filed: Oct. 2, 2009

(86) PCT No.: PCT/US2009/059380
§ 371 (c)(1),
(2), (4) Date: Sep. 14, 2011

(87) PCT Pub. No.: WO2010/040051
PCT Pub. Date: Apr. 8, 2010

(65) Prior Publication Data
US 2012/0177566 A1  Jul. 12, 2012

Related U.S. Application Data

(60) Provisional application No. 61/102,590, filed on Oct. 3, 2008.

(51) Int. Cl.
*A61K 38/00* (2006.01)

(52) U.S. Cl.
USPC ...................................................... 514/19.2

(58) Field of Classification Search
None
See application file for complete search history.

(56) References Cited

U.S. PATENT DOCUMENTS

| | | | | |
|---|---|---|---|---|
| 7,531,515 | B2 * | 5/2009 | Pincus | 514/1.1 |
| 7,745,405 | B2 * | 6/2010 | Pincus | 514/1.2 |
| 2005/0245451 | A1 * | 11/2005 | Pincus | 514/13 |

FOREIGN PATENT DOCUMENTS

| WO | 03/105880 A1 | 12/2003 |
|---|---|---|
| WO | 2009/070650 A1 | 6/2009 |

OTHER PUBLICATIONS

Michl et al., PNC-28, a p53-derived peptide that is cytotoxic to cancer cells, blocks pancreatic cancer cell growth in vivo, 2006, International Journal of Cancer, vol. 119, p. 1577-1585.*
Bowne et al, Cancer Ther. 2007 (available Nov. 15, 2007) 5B pp. 331-344 (numbered as 1-30 in the attached transcript).*
International Preliminary Report on Patentability for PCT/US2009/059380, issued on Apr. 14, 2011.
Written Opinion for PCT/US20091059380, issued on Apr. 8, 2010.
Michl Josef et al: "PNC-28, A p53-derived peptide that is cytotoxic to cancer cells, blocks pancreatic cancer cell growth in vivo" International Journal of Cancer, John Wiley & Sons, Inc, United States, Switzerland, Germany, vol. 119, No. 7, Oct. 1, 2006, pp. 1577-1585, XP002457388 ISSN: 0020-7136.
Sookraj K A et al: "W1961 Novel p53-Derived Peptide Induces Extensive Necrosis in Cancer Cells" Gastroenterology, Elsevier, Philadelphia, PA, vol. 134, No. 4, Apr. 1, 2008, pp. A-743, XP023435265 ISSN. 016-5085 [retrieved on Apr. 1, 2008], (abstract only).
Sookraj K A et al: "Novel p53-derived peptide induces necrosis by membrane-pore formation in pancreatic cancer cells" Journal of the American College of Surgeons, College, Chicago, IL, US, vol. 207, No. 3, Sep. 1, 2008, pp. S97-S98, XP024339480 ISSN: 1072-7515 [retrieved on Aug. 26, 2008], (abstract only).
Bowne W B et al: "p53-derived peptide inhibits human pancreatic cancer cell growth" Journal of the American College of Surgeons, College, Chicago, IL, US, vol. 203, No. 3, Sep. 1, 2006, p. S84, XP025131532 ISSN: 1072-7515 [retrieved on Sep. 1, 2006].
Sarafraz-Yazdi, E. et al.: "PNC-27 and PNC-28 anticancer peptides selectively kill cancer cells by pore formation dependent on the binding of these peptides to hdm2 in cancer cell membranes" 99th AACR Annual Meeting, Apr. 12-16, 2008 Proc Am Assoc Cancer Res vol. 49, No. Abst LB-195, Apr. 2008, Retrieved from the Internet: URL:http://www.aacrmeetingabstracts.org/ [retrieved on Mar. 15, 2010].
Do Tamara N. et al: "Preferential induction of necrosis in human breast cancer cells by a p53 peptide derived from the MDM2 binding site." ONCOGENE, vol. 22, No. 10, Mar. 13, 2003, pp. 1431-1444, ISSN: 0950-9232.

* cited by examiner

*Primary Examiner* — Sheela J Huff
(74) *Attorney, Agent, or Firm* — Hoffmann & Baron, LLP

(57) ABSTRACT

An aspect of the invention provides a method of selectively necrosing cells, comprising: providing a plurality cells, including at least one cancer cell and at least one non-cancerous cell; and administering to the cells a compound, including an HDM-2 targeting component and a cytotoxic component attached to the HDM-2 targeting component, wherein said compound comprises a membrane-active form.

7 Claims, 13 Drawing Sheets

TABLE I & LEGEND

| Cell Line | Plasmid | Percent GFP |
|---|---|---|
| MIA-PaCa-2 | Control Vector (CV) | 43 |
| MIA-PaCa-2 | p53 17-26-V | 45 |
| MIA-PaCa-2 | P53 17-26-scrm-V | 37 |
| BMRPA1 | P53 17-26-V | 30 |

Table I. Efficiency of Transfection of Plasmids into MIA-PaCa-2 and BMRPA1 Cells. FIG. 9

MEMBRANE RESIDENT PEPTIDE IN ANTI-CANCER PEPTIDES CAUSES TUMOR CELL NECROSIS RATHER THAN APOPTOSIS OF CANCER CELLS

CROSS-REFERENCE TO RELATED APPLICATIONS

This patent application is the national stage filing of International Patent Application No. PCT/US2009/059380, filed Oct. 2, 2009, which claims the benefit of and priority to U.S. Provisional Patent Application Ser. No. 61/102,590 filed on Oct. 3, 2008, the contents of which are incorporated herein by reference in their entirety

FUNDING STATEMENT

This invention was made with government support by a Veteran's Administration Grant (WBB) and The American College of Surgeon's Faculty Research Fellowship Award 2007-2009 (WBB).

FIELD OF THE INVENTION

The invention relates to methods of effectively treating various forms of cancer and screening candidate cancer treatments and compounds. Specifically, the present invention is directed to the use of novel compounds and methods to treat cancer and non-cancerous cells and cause necrosis only to cancer cells.

RELATED ART

Cancer treatments which target the p53 protein within the cancer cells have been developed recently. However, some types of cancer cells do not have p53, while others exhibit p53 in a mutated, and/or inactive form. Thus, these p53 targeting cancer treatments are limited since they do not cause cell death in these types of cancer cells. Thus, p53-targeting cancer treatments are ineffective at treating various types of cancer.

SUMMARY OF THE INVENTION

The embodiments of the present invention are directed to the surprising discovery that cancer cells have approximately several times as much HDM-2 in their cellular, mitochondrial, and nuclear membranes than non-cancerous cells. Thus, HDM-2 targeting compounds are successful cancer treatments, causing necrosis to cancer cells while leaving adjacent non-cancerous cells unaffected. HDM-2 targeting treatments thus represent a body of wide-acting cancer treatments that are more effective than the current, limited p53-targeting treatments.

An aspect of the invention provides a method of selectively necrosing cancer cells, but not untransformed or normal cells. The method includes the steps of: administering to the cells a compound, wherein the compound includes an HDM-2 targeting component and a cytotoxic component, where the cytotoxic component may be attached to said HDM-2 targeting component such that the compound comprises a membrane-active form. An example of an HDM-2 targeting component may include, for example, one or more small molecules, a peptide, a protein, a glycoprotein, an antibody (including whole and fragment antibodies), and combinations thereof. Examples of a cytotoxic component may include: a membrane resident peptide (MRP), a toxin, a drug, a radionuclide, an antibody (including whole and/or fragment), and combinations thereof, as may be desired. One or more of the cytotoxic components, including the toxin, drug, radionuclide, antibodies, and combinations thereof, may be known and/or used in the art, for their cytotoxic affects to cells, optionally, cancer cells.

Optionally, the HDM-2 targeting may be a peptide. Where the HDM-2 targeting component and the MRP are both peptides, the MRP is preferably attached to the carboxyl terminal end of the peptide.

Optionally, the method may further include the step of observing the release (from the cancer cell) of an increased LDH amount as compared to an initial LDH amount from the cancer cell, observing necrosis in the cancer cells, and/or observing a non-response in the normal cell. The non-response of a normal cell may indicate that the normal cell is unaffected by the cancer treatment.

Another aspect of the present invention provides a method of causing membranolysis in at least one cancer cell. The method includes the step of administering to at least one cancer cell a compound including an HDM-2 targeting component and a MRP, the MRP attached to the HDM-2 targeting component.

Optionally, the method may further include, for example, observing membranolysis in the cancer cell by microscopy. Observing necrosis of the cancer cell may also be included as a step in the present invention.

Still another aspect of the present invention provides a method of treating cancer in a subject (or patient) in need thereof. The method includes the steps of administering to the subject in need thereof a therapeutically effective amount of a compound having an HDM-2 targeting component and a MRP, the MRP attached to the HDM-2 targeting component. The subject may include, for example, mammals including dogs, cats, chimpanzees, and rats. Optionally, the method may further include the step of correlating a result thereof of the administration step.

Still yet another aspect of the present invention provides a method of screening candidate cancer treatments. The method may include the steps of: providing a plurality of cancerous cells; administering a candidate cancer treatment to the plurality of cancerous cells; and measuring the level of LDH released from said cells. LDH is measurable in the cell medium, once it is released from the cells.

Optionally, the method includes administering the candidate cancer treatment which may include a compound including an HDM-2 targeting component and an MRP. As the method employs screening compounds for their potential abilities as (1) binding affinity for HDM-2 and (2) membrane transport character, one or both of these characteristics may be desired in various drug candidates that are screened with the present method. The screening process, may aid in identifying components that act within the desired parameters and with the preferable characteristics as effective cancer treatments. Additionally desirable characteristics of cancer treatment, including causation of membranolysis and ultimately, cancer cell necrosis may be observed or otherwise measured after each candidate compound is administered. Thus, the efficacy of each candidate may be screened.

Optionally, the method may also contain the steps of observing the cells for LDH, and/or correlating the level of LDH in the cellular medium to a standard. Thus, necrosis, and the level thereof may be identified for each candidate, as it may correlate to the level and/or amount of LDH released for a given sample.

Still yet another aspect of the present invention provides a method of selectively necrosing cancer cells, including the steps of: providing at least one cancer cell and at least one non-cancerous cell; and contacting the cells with a compound, where the compound includes an HDM-2 targeting compound having an MRP attached thereto, wherein the compound binds to a cancer cell membrane and configures to a membrane active form, binding to the cancer cell membrane. This binding site is preferably at a site of HDM-2, and results in trans-membrane pore formation in the cancer cell membrane.

The method optionally includes the steps of measuring a level of LDH from the cancer cell, observing necrosis of the cancer cell, and/or observing a non-result in the non-cancerous cell as a result of the administering step.

A further aspect of the present invention provides a method of identifying cancer cells from a plurality of cells, including: providing a plurality of cells, wherein at least one of the cells is a candidate cancer cell; administering to the plurality of cells an HDM-2 recognition compound; and observing the plurality of cells for the HDM-2 recognition compound to bind to a cell membrane of at least one of the cells, where binding to the cell membrane is indicative of a cancerous cell.

Optionally, the method may include the step of fluorescing the HDM-2 recognition molecule with an observable agent. The observable agent may include, for example, various known dyes, enzyme-substrate combinations, radiopaque materials, fluorescing agents, and combinations thereof. The observable agents may be visually observable, observable with filtered light through various scopes, and/or indentified through X-ray and or other medical instrumentation photography. With HDM-2 targeting compounds used in conjunction with observable agents, cancerous areas may be indentified, topographically mapped, and better understood than with previous cancer identification and visualization techniques.

The method may further include the step of classifying an identified cancer cell as a type of cancer. This may be done in vivo, as part of a diagnostic for cancer. Alternatively, the fluorescent-labeled MRP attached to an HDM-2 targeting component or HDM-2 recognition agent may be administered to a candidate surgical area. Such a use may provide derivative identifiers to a surgeon of the highly cancerous tissue, less cancerous tissue, and non-cancerous tissue for surgical removal and/or intervention purposes. As such, the embodiments and features of the present invention may provide a great aid in surgical pathology, helping pathologists to distinguish cancer from non-cancer.

The description of the elements and features of the present invention and equivalents thereof may be better understood through a study of the following drawings, description, and claims.

BRIEF DESCRIPTION OF THE DRAWINGS

FIG. 9 depicts a table summarizing the efficiency of transfection of plasmids into MIA-PaCa-2 and BMRPA1 cells.

Figure 1:
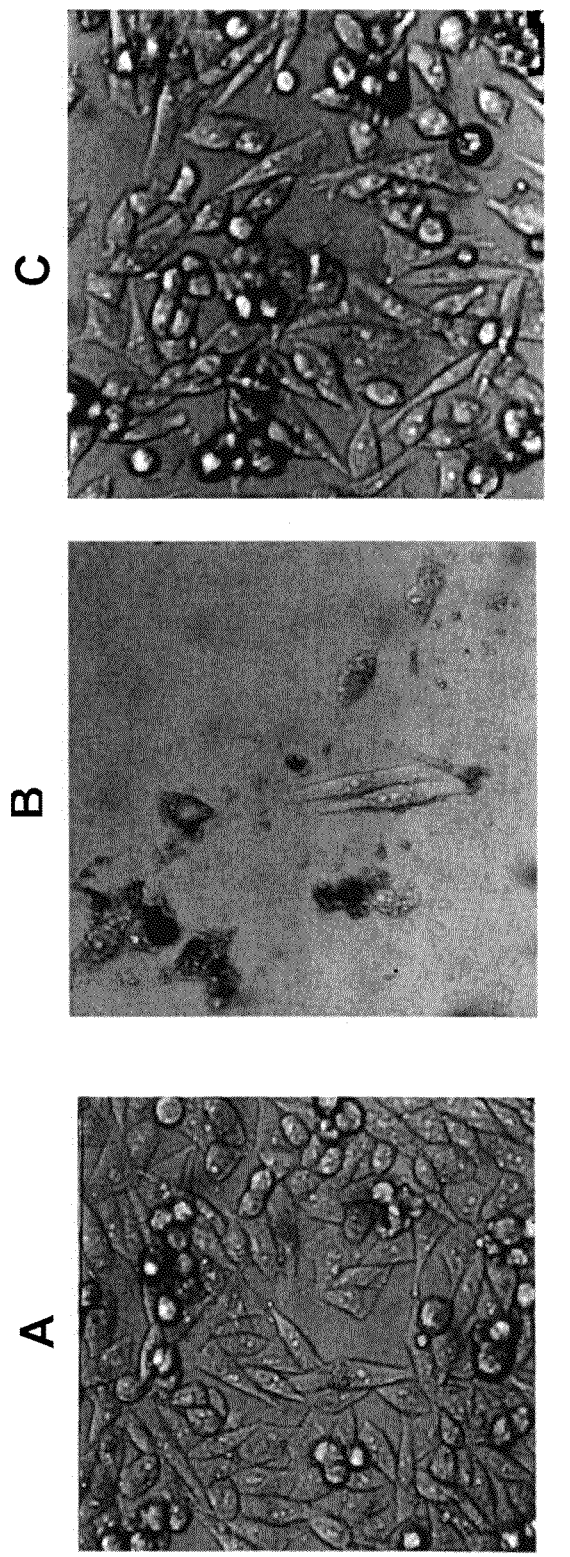
FIG. 1 is experimental data which illustrates that PNC-28 is cytotoxic to MiaPaCa-2 cells. Panel A shows untreated MiaPaCa-2 cells incubated for 24 h. Panel B represents MiaPaCa-2 cells treated for 24 h with 75 μmol/ml of PNC-28. Panel C shows MiaPaCa-2 cells treated with 75 μmol/ml PNC-29 negative control peptide for 48 h.

DETAILED DESCRIPTION OF THE INVENTION p53 is the gene that is most commonly disrupted in cancer. p53 acts as the guardian of the genome, as it guards against copying of the DNA. It was previously established that p53 gene within the cells was a target treatment for cancer. However, p53 targeting treatment in cancer cells has various problems associated with it that limits the use of p53 targeting treatments. For example, not all cancers exhibit p53 in the cell. Targeting treatments for these types of cancers would not work, as there is no p53 for the targeting compounds to bind to. Also, some cancers exhibit a mutated form of p53, which is inactive. As the p53 is inactive in these cancers, targeting compounds also do not work for these cancers. Thus, p53 dependent treatment mechanisms are ineffective against these types of cancer.

The materials and methods of the present invention provide novel methods of treatment that are directed to a common characteristic in many various forms of cancer. Such materials and methods may be used as a targeted treatment to many various forms of cancer, which, up until now, may have very different and less effective and predictable treatment options and avenues. These new methods, materials, and screening methods provide effective treatments, screening methods for additional novel drug candidates, and other benefits and advantages over the current medical technology.

As used herein, cancer includes any disease or disorder associated with uncontrolled cellular proliferation, survival, growth, or motility. Cancers that may be treated or prevented by the present invention include any cancer whose cells have increased expression of HDM-2 in their plasma membranes. Such cancers may include, for example, pancreatic cancer, breast cancer, colon cancer, gastric cancer, prostate cancer, thyroid cancer, ovarian cancer, endometrial cancer, glioblastoma, astrocytoma, renal carcinoma, lung cancer, sarcoma, including osteogenic sarcoma, mesothelioma, sporadic non-familial tumors, lymphoma, and others including hematologic cancers such chronic myelogenous leukemia. Precancerous conditions, where cells exhibit high amounts of HDM-2 in the plasma membrane, are also included as treatable with the compositions and methods of the present invention.

The present invention is directed to the surprising discovery of the inventors that cancer cell membranes and nuclear membranes have a large amount of HDM-2 as compared to normal non-cancerous cells. HDM-2 and MDM-2 (human double minute vs. mouse double minute) each have a p53 binding domain. HDM-2 and MDM-2 are found in the cell and nuclear membranes of cancer cells, but not in normal, healthy cells. The compounds of the present invention include a HDM-2 targeting component and a Membrane Resident Peptide (MRP), where the MRP is attached to the carboxyl terminal end of the HDM-2 targeting component. The MRP may include the residues that are shared by the p53 binding domain (or region) of HDM-2. As such, when the compound is administered or otherwise contacted to at least one cancer cell, the HDM-2 targeting component, which has a p53 binding domain, may bind to the HDM-2 in the cancer cell membrane. The presence of the MRP on the end allows the compound to become membrane-active and to form well-defined pores in the cell membrane (membranolysis), which allow for extrusion of the intracellular contents and compromise the integrity of the cell. Pores in the cancer cell membrane are formed as an immediate result of administration of the compound. After the pores are formed, cell necrosis, or cell death, results within a short time frame. Thus, cancer treatments having an HDM-2 targeting component and an MRP are effective treatments for cancer.

Cancer cells have approximately five times as much HDM-2 as normal cells in their cellular membranes and nuclear membranes. Though the cancers may not exhibit similar characteristics or typical treatment avenues, as many cancers each have HDM-2 in their cell membranes, these cancers are likewise susceptible to the methods of treatment of the present invention. Cancers that have been identified as having a large amount of HDM-2 in the cell membrane include, for example: MIA-PaCa-2 human pancreatic cancer cells, MCF-7 human breast cancer cells, B 16 mouse melanoma, and a human melanoma cell line A2025. The compounds which have both an HDM-2 targeting component and an MRP thus have a high affinity for cancer cells, and will thus only bind to and cause necrosis of cancer cells when administered to a combination of cancer cells and normal, healthy cells.

The present inventors have discovered methods and uses of the compounds containing an HDM-2 binding domain having a MRP attached at its end, where the compound is specifically designed to target cancer cells and not target normal, healthy cells of a sample. Where both the HDM-2 targeting component and the MRP are peptides, the MRP is desirably attached to the carboxyl terminal end of the HDM-2 targeting component.

Thus, these methods may be used to treat a sample of cells containing both healthy, normal cells and cancer cells. Such samples would include cell lines, tissue samples, tumors, and/or a subject having cancer in need of treatment. As the methods of treatment do not cause cell death of normal cells, these methods of treatment are focused on the cancer cells, irrespective of the mode of administration to the cell sample. Thus, these methods of treatment may be used for tumors or cancers that are widespread, inoperable, or otherwise not easily treated with conventional means or combination therapies.

The methods of the present invention kill cancer cells by necrosis. Necrosis is induced by the combined action of the compound, which acts both to bind to HDM-2 and to form pores on the cellular membrane. The pores ultimately cause the cell membrane to lose its integrity such that intracellular contents leak from the cell, and the cell undergoes necrosis.

The present invention provides methods of using HDM-2 targeting cancer compounds which correspond to all or a portion of amino acid residues 12-26 of human p53 protein. When fused to a MRP, the peptides are lethal to malignant or transformed cells. The subject cancer treatment compounds may be useful in treating neoplastic disease in an animal, preferably a human.

The compounds of the present invention may include, for example, PNC-27 and PNC-28. Additionally, one or more compounds may be used, where a compound may have an HDM-2 targeting component. The HDM-2 targeting components may be, for example, the residues of p53 which bind to HDM-2. Further, the compound may include a membrane resident peptide, or, MRP. Both PNC-27 and PNC-28 are examples of p53-derived peptides from the human double minute binding domain (HDM-2) that are attached to MRP. These compounds induce tumor cell necrosis of cancer cells, but not normal cells. The anti-cancer activity and mechanism of PNC-28 (p53 aa17-26-MRP) was specifically studied by the inventors of the present invention as against human pancreatic cancer, though uses and applications are included with the various methods of the present invention.

The inventors show with the present invention and supporting experimental examples that the MRP is necessary for this action since expression of the naked p53 sequence without MRP in cancer cells causes wild-type p53-dependent apoptosis, or programmed cell death, not tumor cell necrosis.

Preferably, the MRP includes predominantly positively charged amino acid residues since a positively charged leader sequence, which may stabilize the alpha helix of a subject peptide. Examples of MRPs which may be useful to the HDM-2 targeting compounds of the present invention are described in Futaki, S. et al (2001) Arginine-Rich Peptides, J. Biol. Chem. 276, 5836-5840, and include but are not limited to the following MRPs in the TABLE 1, below. The MRP may be, for example, peptides included in SEQ ID NO:1, or 9-29. The numbering of the amino acid residues making up the MRP is indicated parenthetically immediately after the name of the component in most of the examples in most of the sequence listings.

TABLE I

| SEQ ID NO: | Sequence | NAME |
|---|---|---|
| SEQ ID NO: 1 | KKWKMRRNQFWVKVQRG | Membrane resident peptide (MRP), reverseomer of Antennapedia |
| SEQ ID NO: 2 | PPLSQETFSDLWKLLKKWKMRRNQFWVKVQRG | PNC-27 |
| SEQ ID NO: 3 | ETFSDLWKLLKKWKMRRNQFWVKVQRG | PNC-28 |
| SEQ ID NO: 4 | MPFSTGKRIMLGEKKWKMRRNQFWVKVQRG | PNC-29 |
| SEQ ID NO: 5 | MPFSTGKRIMLGE | peptide from cytochrome P450 (aka "X13") |
| SEQ ID NO: 6 | TIEDSYRKQVVIDKKWKMRRNQFWVKVQRG | PNC-7 |
| SEQ ID NO: 7 | TIEDSYRKQVVID | ras-p21 residues 35-47 |
| SEQ ID NO: 8 | PPLSQETFSDLWKLL | PNC-26, residues 12-26 of the HDM-2 binding domain of p53 |
| SEQ ID NO: 9 | YGRKKRRQRRRPPQ | HIV-1 TAT(47-60), membrane resident peptide |
| SEQ ID NO: 10 | GRKKRRQRRRPPQ | D-TAT, membrane resident peptide |
| SEQ ID NO: 11 | GAAAAAAAAAPPQ | R-TAT G(R)$_9$PPQ, membrane resident peptide |
| SEQ ID NO: 12 | PKKKRKV | SV40-NLS, membrane resident peptide |
| SEQ ID NO: 13 | KRPAAIKKAGQAKKKK | nucleoplasmin-NLS, membrane resident peptide |
| SEQ ID NO: 14 | TRQARRNRRRRWRERQR | HIV REV (34-50), membrane resident peptide |
| SEQ ID NO: 15 | RRRRNRTRRNRRRVR | FHV (35-49) coat, membrane resident peptide |

TABLE I-continued

| SEQ ID NO: | Sequence | NAME |
|---|---|---|
| SEQ ID NO: 16 | KMTRAQRRAAARRNRWTAR | BMV GAG (7-25), membrane resident peptide |
| SEQ ID NO: 17 | TRRQRTRRARRNR | HTLV-II REX 4-16, membrane resident peptide |
| SEQ ID NO: 18 | KLTRAQRRAAARKNKRNTR | CCMV GAG (7-25), membrane resident peptide |
| SEQ ID NO: 19 | NAKTRRHERRRKLAIER | P22 N (14-30), membrane resident peptide |
| SEQ ID NO: 20 | MDAQTRRRERRAEKQAQWKAAN | LAMBDA N(1-22), membrane resident peptide |
| SEQ ID NO: 21 | TAKTRYKARRAELIAERR | Phi N (12-29), membrane resident peptide |
| SEQ ID NO: 22 | TRRNKRNRIQEQLNRK | YEAST PRP6 (129-124), membrane resident peptide |
| SEQ ID NO: 23 | SQMTRQARRLYV | HUMAN U2AF, membrane resident peptide |
| SEQ ID NO: 24 | KRRIRRERNKMAAAKSRNRRRELTDT | HUMAN C-FOS (139-164), membrane resident peptide |
| SEQ ID NO: 25 | RIKAERKRMRNRIAASKSRKRKLERIAR | HUMAN C-JUN (252-279), membrane resident peptide |
| SEQ ID NO: 26 | KRARNTEAARRSRARKLQRMKQ | YEAST GCN4, membrane resident peptide |
| SEQ ID NO: 27 | KLALKLALKALKAALKLA | Example membrane resident peptide (MRP) |
| SEQ ID NO: 28 | LLIILRRRIRKQAKAHSK | p-vec, membrane resident peptide |
| SEQ ID NO: 29 | RRRRRRRR | $(Arg)_8$ or any poly-R from $(R)_4$-$(R)_{16}$, membrane resident peptide |
| SEQ ID NO: 30 | GCCACCATGG | Kozak sequence |
| SEQ ID NO: 31 | AGTCGAATTCGCCACCATGGAAACATTTTCAG ACCTATGGAAACTACTTTGAGCGGCCGCAGTC | sense strand sequence of cDNA encoding the p53 17-26 sequence |
| SEQ ID NO: 32 | ETFSDLWKLL | residues 17-26 of HDM-2 binding domain of p53 |

Other MRP materials may also be used. Such sequences are described e.g., in Scheller et al. (2000) Eur. J. Biochem. 267:6043-6049, and Elmquist et al., (2001) Exp. Cell Res. 269:237-244, the contents of which are incorporated herein by reference in its entirety.

Desirably, the positively charged MRP may include the amino acid sequence: KKWKMRRNQFWVKVQRG (SEQ ID NO: 1), which is related to the reverseomer sequence of the antennapedia sequence. Preferably, the MRP is attached to the carboxyl terminal end of a subject compound (e.g. peptide).

Cell death can occur by either necrosis or apoptosis. p53-targeting treatments typically cause cell death through apoptosis, while the compounds and methods of the present invention cause cell death by necrosis. Necrosis is not genetically controlled, while apoptosis is genetically controlled. Apoptosis is the deliberate cellular response to specific environmental and developmental stimuli or programmed cell death. Cells undergoing apoptosis exhibit cell shrinkage, membrane blebbing, chromatin condensation and fragmentation. Necrosis involves the destruction of cytoplasmic organelles and a loss of plasma membrane integrity. Though apoptosis does not have the inflammation which results when cancer cells die through necrosis, p53 targeting treatments fail to treat those cancers that do not exhibit p53, or, through mutations, exhibit an inactive p53 form that is unresponsive to p53 targeted treatments. After the DNA damage in the caspase enzyme pathway, there are a series of events which occur that involve calcium activation and calpain enzymes which further leads to other cellular changes and regulation of cytoplasmic enzymes. During p53-dependent apoptosis, there is a sequential expression of annexin V-binding membrane phospho-Serine, Bax waf$^{p21}$, and caspases; these proteins are used as markers for p53-dependent apoptosis.

A major difference between necrosis and apoptosis in vivo is the complete elimination of the apoptotic cell before an inflammatory response is seen. Necrosis usually causes inflammation. Though apoptosis can be thought of as a clean and neat process, the p53 targeting treatments do not result in apoptosis in all types of cancer cases. Though necrosis may typically cause an inflammatory response to a treatment site directed at targeting HDM-2, HDM-2-targeting treatments are more effective against various forms of cancer, including those where p53 is not present in the cancer cells, or where p53 is in a mutated or an inactive form.

Human pancreatic cancer cells, MiaPaCa-2 cells, were treated with PNC-28. Necrosis was determined by measuring lactate dehydrogenase (LDH) as well as elevation of pro-apoptotic proteins. Mutant PNC-compound (PNC-29) and HDM-2-binding domain p53 aa12-26 without MRP (PNC-26) were controls. PNC-29 and PNC-26 are both used as controls, as PNC-29 includes a non-p53 peptide bound to the MRP, and PNC-26 includes aa 12-26 of the p53 binding domain but no MRP.

Since the inventors have discovered evidence that MRP is required for anti-cancer activity, the inventors of the present invention tested "naked" p53 peptide without MRP by transfecting a plasmid that encodes p53 aa17-26 segment of PNC-28 into MiaPaCa-2 and an untransformed rat pancreatic acinar cell line, BMRPA1. Time-lapse electron microscopy was employed to further elucidate anti-cancer mechanism.

The inventors acquired the following results from the above experiment. Treatment with PNC-28 does not result in the elevation of pro-apoptotic proteins found in p53-induced apoptosis, but elicits rapid release of LDH, which is indicative of tumor cell necrosis. Accordingly, using transmission electron microscopy, the inventors of the present invention observed membrane pore formation and dose-dependent killing. In direct contrast, MiaPaCa-2 cells, that were transfected with a vector expressing p53 aa 17-53, as in PNC-28, underwent apoptosis, and not necrosis, as evidenced by expression of high levels of caspases-3, 7 and annexin V with background levels of LDH.

These results suggest that PNC-28 may be effective in treating human pancreatic cancer. More particularly, these results suggest that compounds having an HDM-2 binding domain which is attached to an MRP at the carboxyl terminal end may be effective in treating human pancreatic cancer. The MRP appears responsible for the fundamental change in the mechanism of action inducing rapid necrosis initiated by membrane pore formation. Cancer cell death by apoptosis was observed in the absence of MRP. Thus, PNC-28 and compounds of similar form and function will cause cancer cell necrosis by a cell membrane pore formation mechanism, rather than a p53 targeted treatment within the cell, which causes necrosis.

The inventors of the present invention have developed two peptides, PNC-27 and PNC-28, that contain p53 protein residues 12-26 and 17-26, respectively, attached to a MRP. Although originally conceived to block the binding of p53 to HDM-2 in cancer cells, thereby increasing the half-life of p53 preventing its ubiquitination and proteosomic degradation, it was determined that these compounds caused cancer cell death even in cells that lacked p53 expression (1,3). The principals further observed that in cancer cells treated with these compounds, there was no increase in expression of p53-induced pro-apoptotic proteins such as caspase and Bax (1-3). Rather, these compounds induced tumor cell necrosis as evidenced by the rapid release of lactate dehydrogenase (LDH) from treated cancer cells (2, 3).

Interestingly, fluorescent probe-labeled PNC-27 was detected at early stages after treatment in the cell and nuclear membranes (2). Time-lapse electron microscopy studies later revealed that both compounds induced pore formation in the cell and nuclear membranes, consistent with the compounds being membrane active (2). Furthermore, consistent with this activity, the three-dimensional structure of PNC-27 by two-dimensional NMR was determined to be an amphipathic alpha-helix-loop-alpha-helix, a structural motif similar to that of a number of membrane-active peptides (4, 5). Importantly, the principals devised a double-fluorescent-labeled PNC-27 that contained a green fluorescent probe (fluorescein isothiocyanate, i.e., FITC) on the amino terminal end and a red fluorescent probe (rhodamine) on the carboxyl terminal end (MRP-end). When this double-labeled PNC-27 was incubated with MIA-PaCa-2 and MCF-7 cancer cells, a high density of yellow fluorescence confined to the cell membrane after 1 hour of incubation was identified. The only manner in which yellow fluorescence could be obtained is if the amino and carboxyl terminal ends of the compound stay together, i.e., there is no splitting of PNC-27 into HDM-2 targeting and MRP portions/components. During this time, there is a maximal release of LDH into the incubation medium, indicating maximal cell membrane damage. Thus the full PNC-27 compound is required for cell membrane lysis and cancer cell death.

Though these compounds induce tumor cell necrosis among a wide range of different human tumors, including TUC-3 metastatic pancreatic cancer cells (6), they remarkably have no effect on the growth and viability of a number of normal cell lines. These include rat pancreatic acinar cells, called BMRPA1 (1,3), the normal counterpart of TUC-3 cells, human breast epithelial (MCF-10-2A) cells (2), and cord blood-derived human stem cells (1). These compounds also have no effect on the growth or viability of human keratinocytes and human fibroblasts. As previously shown, both compounds appear to induce the killing of cancer but not normal cells by a novel membranolytic mechanism (2).

In contrast, several studies (7-12) reported p53-dependent apoptosis of treated cancer cells when synthesized peptide sequences targeted to bind to intranuclear HDM-2 were attached to leader sequences on their amino terminal ends. In one such study (12), twelve residues from the h (or m) dm-2 binding domain of p53 were synthesized and attached at their amino termini to a TAT leader peptide. This peptide was found to induce apoptosis of uveal melanoma and retinoblastoma cell lines, both containing wild-type p53. Although active against cell lines homozygous for mutant p53, this peptide was not tested against p53-null cells. Interestingly, placement of the MRP on the amino terminal end of the p53 17-26 peptide resulted in a marked diminution in the cytotoxicity of the compound to cancer cells (M Kanovsky, M R Pincus & J Michl, unpublished observations).

Since PNC-27 and PNC-28 both contain p53 sequences involved in the binding of p53 to HDM-2 but induce cancer cell death via membranolysis in a p53-independent manner and display a structural motif of a membrane active component that depends on the presence of the MRP on the carboxyl terminal end of the p53 sequence, the present inventors inquired as to whether MRP plays an essential role in the membranolytic activity of these compounds.

To investigate this question, the "naked" p53 17-26 peptide, i.e., with no MRP, was introduced into a human pancreatic cancer cell line, MiaPaCa-2, by transfecting a plasmid encoding this peptide into these cells in which peptide expression occurs. The inventors also treated these cells with PNC-28. In both conditions, the inventors measured expression of markers for apoptosis and necrosis to explore whether the naked peptide induces apoptosis in contrast to the same peptide linked to MRP on its carboxyl terminal end (which induces necrosis).

PNC-28, but not Negative Control Peptide PNC-29, is Cytotoxic to MiaPaCa-2 Cells.

PNC-28 was incubated with $6\times10^6$ Mia-PaCa-2 cells for 5 days at concentrations ranging from 12.5-75 μmol/ml. The anti-cancer effect on MiaPaCa-2 cells incubated with PNC- 28 is shown in FIG. 1(A-C). FIG. 1A demonstrates untreated MiaPaCa-2 cells that are not contact-inhibited and spindle-shaped, many becoming multinucleated. After 24 h of treatment with 75 μmol/ml PNC-28, these cells appear necrotic demonstrated by membrane blebbing and disruption, forming cell clumps coalescing into aggregates of cellular debris (FIG. 1B). At 48 h, there was near 100 percent cell death as measured by trypan blue dye uptake. In contrast, negative control peptide PNC-29 at 75 μmol/ml had no effect on cellular growth, morphology, and viability (FIG. 1C). Thus, FIGS. 1A through 1C illustrate that peptide sequence that correlates to p53 aa residues 17-26 (PNC-28 peptide sequence) with the MRP, as opposed to non-p53 peptide sequence with MRP, causes necrosis, resulting in mere cell clumps and cellular debris when administered to the human pancreatic cancer cell line MiaPaCa-2. Thus, the MRP causes pore formation in the membrane of cancer cells when in combination with a p53 aa residue, which binds to HDM-2 in the cell membrane.

Figure 2:
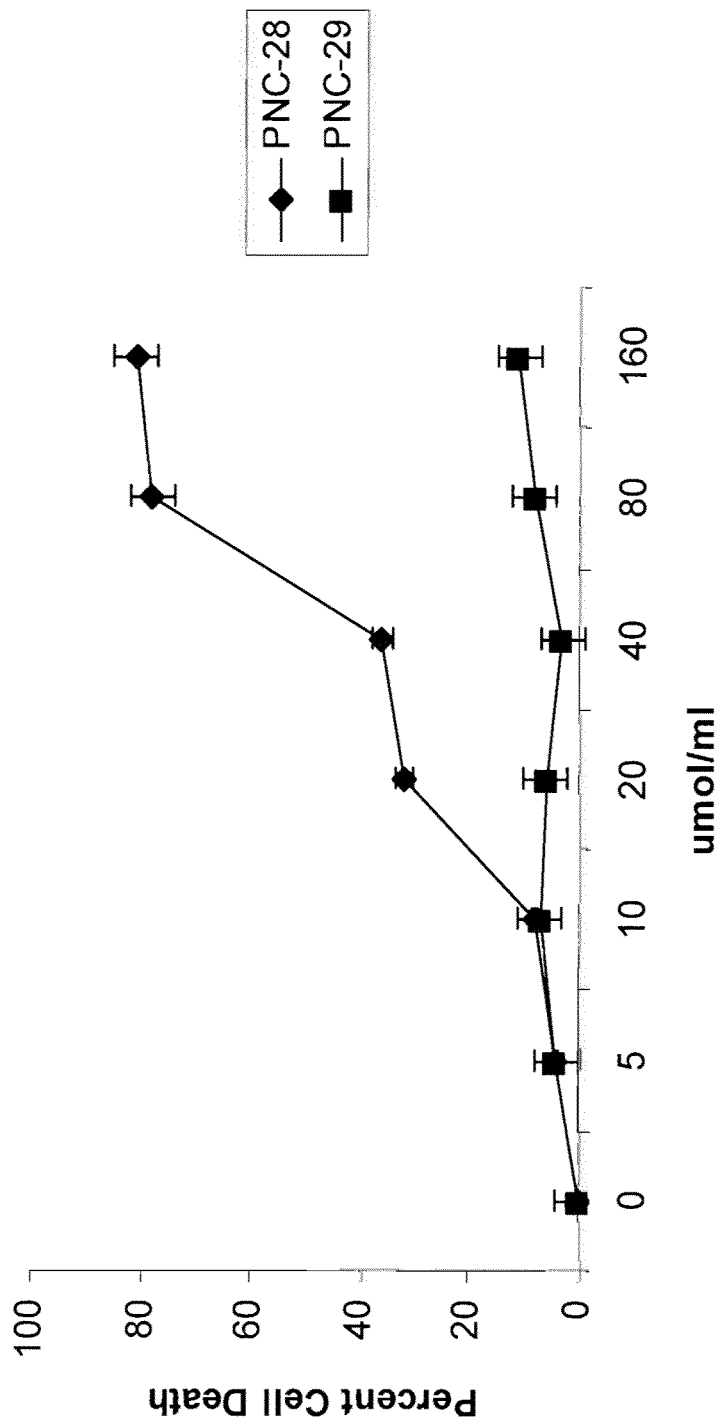
FIG. 2 is a chart of experimental data which illustrates that PNC-28 (diamonds) is cytotoxic to MiaPaCa-2 cells in a dose-dependent manner over a dose range of 0 μmol/ml up to 160 μmol/ml. Specifically, a dosage of 20 μmol/ml caused roughly 35% cell death, while a dosage of 80 μmol/ml caused over 80% cell death at 48 h. The effect of the negative control PNC-29 (squares) is also shown. The effective dose range for PNC-28 at 48 h from 20 to 80 μmol/ml is strongly statistically significant ($P<0.001$).

In FIG. 2, inhibition of proliferation was obtained after only 48 h of peptide treatment. The effective compound dose ranged between 20 and 75 μmol/ml. It should be noted that doses of PNC-28 between 20 and 75 μmol/ml induced virtually 100 percent cell death; the times required for cell killing decreased as dose increased. For example, 80 mmol/ml induced near total cell death in 48 h while 40 μmol/ml induced similar cell death in 4 days, and 20 μmol/ml induced cell death in 1 week. FIG. 2 illustrates that, as the dosage of compound PNC-28 increases, so too does the percent of cell death measured in a 48 hour period. While it is possible to administer a dosage above 160 μmol/ml, the cancer cells will not be necrosed at any greater of a speed. Thus, 160 μmol/ml is the desired upper limit of the dosage for the cell sample sized used with these experiments.

Figure 3:
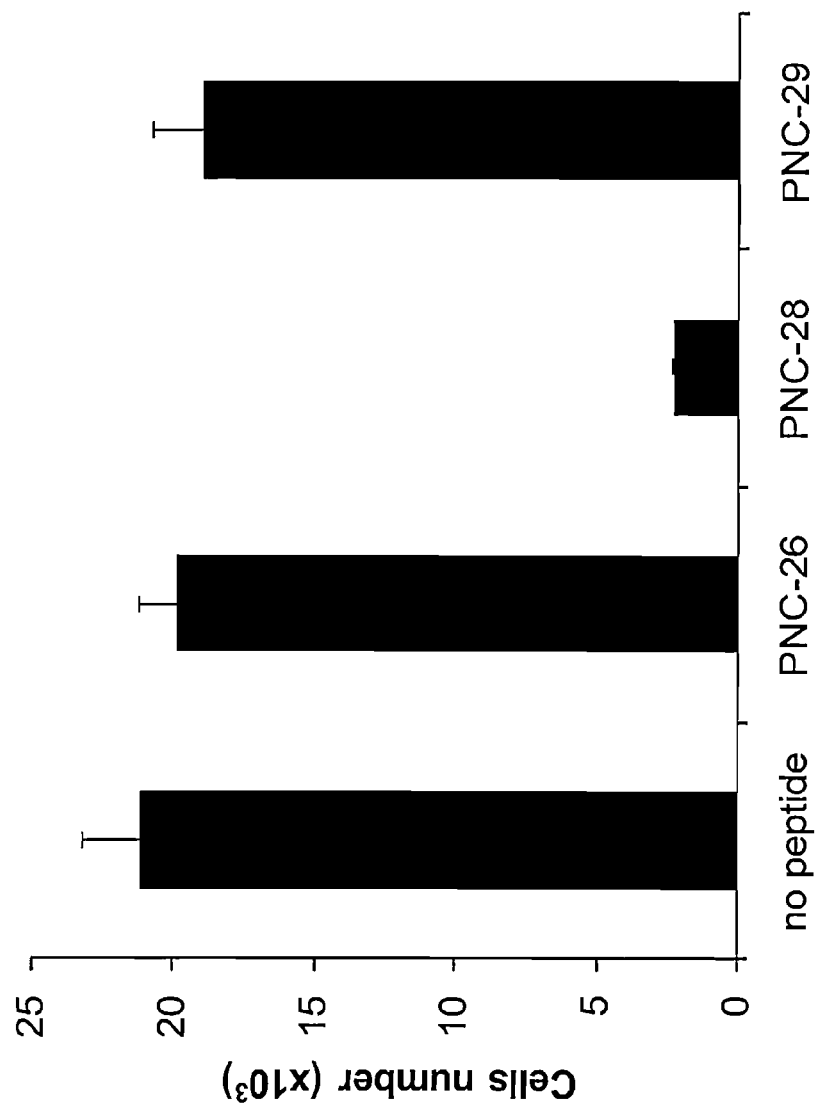
FIG. 3 is a chart of experimental data which illustrates that the carboxyl terminal attached MRP to residues 17-26 (PNC-28) is required for cytotoxicity to cancer cells. The chart depicts the number of remaining cells after 48 hours have passed, shown as a function of treatments administered. MiaPaCa-2 cell death following treatment with no peptide (condition 1), 75 μmol/ml of PNC-28 (condition 3), PNC-26 (condition 2), and negative control PNC-29 (condition 4) after 48 h of treatment.

FIG. 3 summarizes the cytotoxic effects on Mia-PaCa-2 cells of PNC-28 but not control compounds including PNC-29 and the "naked" p53 17-26 peptide (without the MRP), PNC-26, which cannot traverse the cell membrane since it lacks the MRP. Since PNC-29 contains the MRP, but not the p53, sequence and has no effect on cell growth, the MRP itself does not induce the observed cytotoxicity. FIG. 3 illustrates that the number of cells in the sample untreated as compared to treated with the two controls is relatively the same; in contrast, PNC-28 cell death of cytotoxicity is far greater than the negative controls and control. Thus, to cause necrosis by the proposed HDM-2 mechanism, the compound preferably includes both an HDM-2 binding site (HDM-2 targeting component) and a MRP.

As a further control, the inventors' original experiment (1) by incubating 75 μmol/ml PNC-28 with untransformed BMRPA1 acinar cells (1) and with the untransformed breast epithelial cell line, MCF-10-2A (2). There was no growth inhibition or cytotoxicity found (data not shown; see refs. 1 and 2). These results suggest that PNC-28 is lethal specifically to cancer cells and does not interfere with normal cell growth, as concluded in the inventors' previous studies (1,2).

Markers for Necrosis and Apoptosis in MiaPaCa-2 Cells Treated with PNC-28.

Figure 4A:
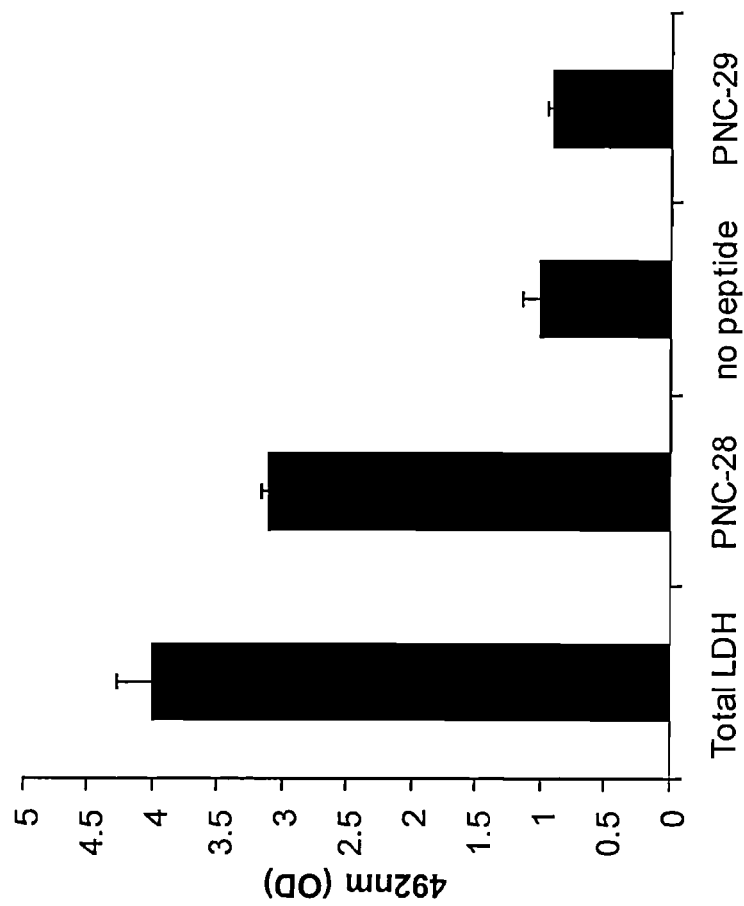
FIG. 4A is a chart of experimental data which illustrates that PNC-28 induces cellular death by necrosis in MiaPaCa-2 cells. LDH activity (measured as absorbance/optical density at 492 nm) was recorded for MiaPaCa-2 cells incubated with 25 μmol/ml of PNC-28 (condition 2), no peptide (condition 3), and PNC-29 (condition 4) at 24 h. Maximal LDH release is shown after treatment with known lysis buffer (condition 1).

In previous studies by the present inventors, it was found that PNC-28 induced cancer cell death in a variety of human cancer cells (1,2) by inducing tumor cell necrosis rather than apoptosis (2). This was manifested in baseline expressions of caspase but high levels of LDH within 24 h in the medium indicative of membrane lysis. Therefore, the expression of LDH and caspase in MiaPaCa-2 cells treated with PNC-28 was investigated. FIG. 4A shows that LDH activity is elevated in cells treated with PNC-28 (condition 2) almost to the same extent as cells that were lysed with lysis buffer (condition 1). On the other hand, only baseline levels of LDH were found for cells treated with negative control PNC-29. As is shown in FIG. 4A, when PNC-28 is administered to cancer cells, it exhibits similar lysis causing conditions as the administration of a lysis buffer; whereas the PNC-29 which has no HDM-2 binding domain and does not cause lysis (and exhibits an optical density closer to the control where no compound—or peptide—is administered). Along the Y axis, OD refers to optical density, or absorption, of LDH, the necrosis indicating factor.

Figure 4B:
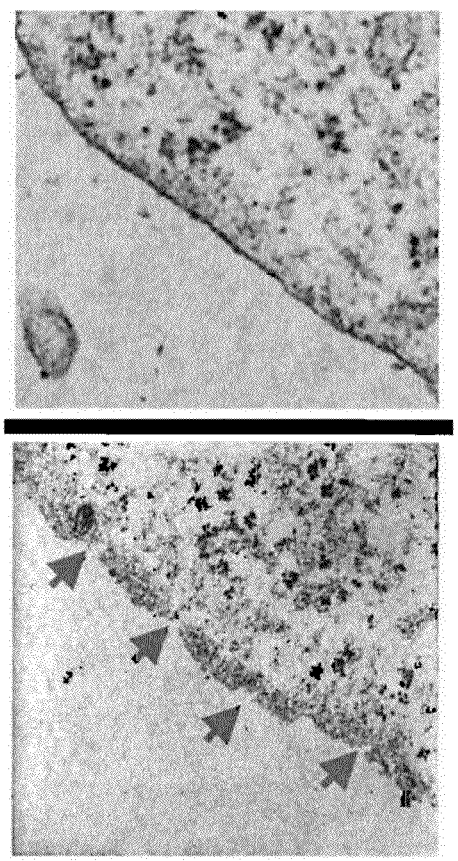
FIG. 4B is experimental data which illustrates comparative electron micrographs of MiaPaCa-2 cells that were untreated (right panel) versus treated (left panel) with 25 μmol/ml PNC-28 for 15 min. The arrows in the left panel point to gaps or holes in the cell membrane induced by PNC-28.

The premise that PNC-28 induced tumor cell necrosis is supported by electron micrographs of MiaPaCa-2 cells treated with this compound in a study that is identical to the one performed on breast cancer cells by the present inventors (2). As shown in FIG. 4B, MiaPaCa-2 cells treated with PNC-28 (left panel) exhibit lysis of their plasma membranes as previously determined for breast cancer cell lines (2), in contrast to untreated cells (right panel) that have their plasma membranes intact. This pattern is characteristic of tumor cell necrosis (2). Thus, PNC-28 is able to both bind to the cell membrane and also transport at least part of the compound molecule through the cell membrane, which results in the pore formation, or lysis, shown in FIG. 4B.

Figure 4C:
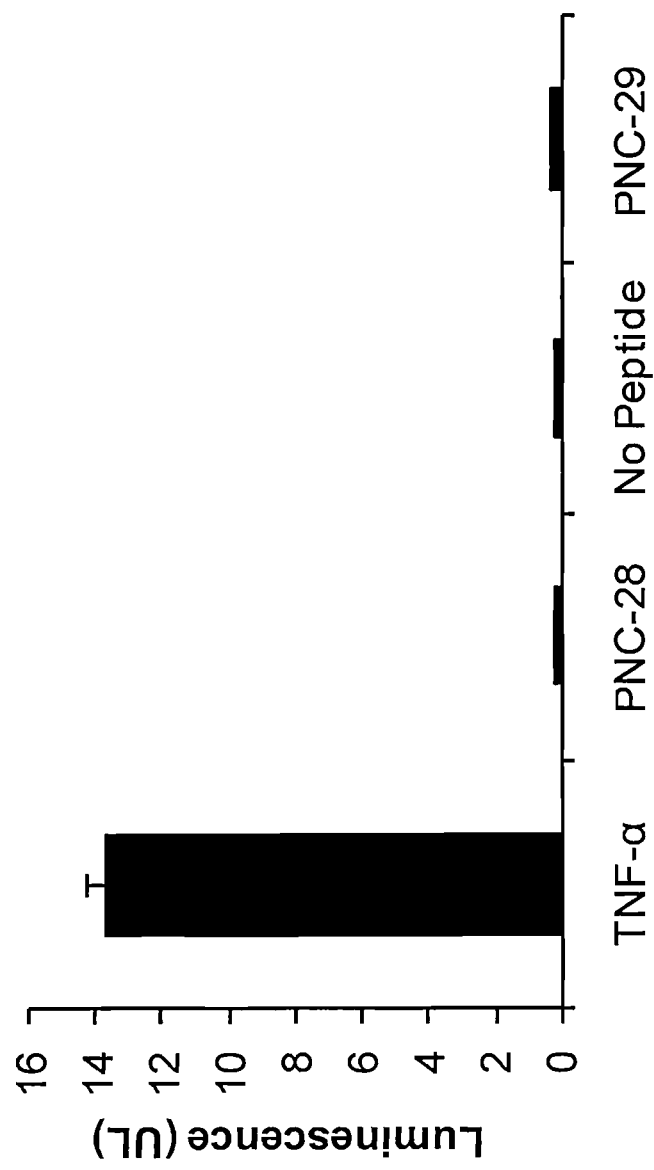
FIG. 4C is a chart of experimental data which illustrates that PNC-28-induced cell death not caused by apoptosis. Caspase 3 activity, an apoptosis indicator, was recorded for MiaPaCa-2 cells incubated with 25 μmol/ml of PNC-28 (condition 2), no peptide (condition 3), and PNC-29 (condition 4) at 24 h. Maximal caspase release is shown after treatment with TNF-α (condition 1) known to induce apoptosis. Caspase 3 activity is measured by luminescence (UL), as shown on the y-axis.

In contrast, as can be seen in FIG. 4C, only baseline levels of caspase were expressed in MiaPaCa-2 cells treated with PNC-28 and were identical to the level expressed in cells treated with control, PNC-29. This finding confirms the conclusion that PNC-28 does not induce apoptosis. Thus PNC-28 induces tumor cell necrosis in MiaPaCa-2 cells as found for other cancer cell lines (1,2). TNF-α is a necrosis inducing agent. On the Figure, UL refers to units luminescence, or luminescence intensity.

Figure 4D:
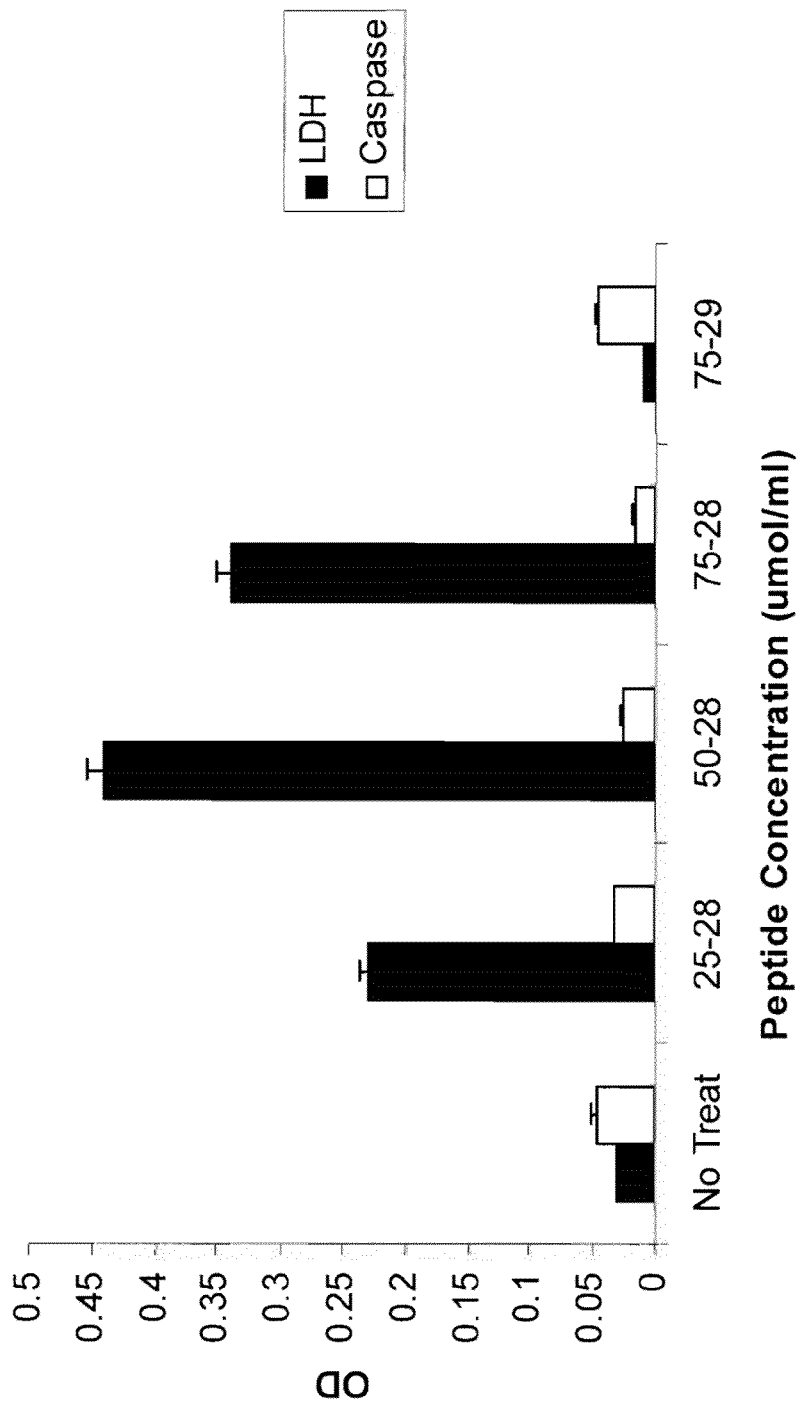
FIG. 4D is a chart of experimental data which illustrates that PNC-28 induces cell death by causing tumor cell necrosis, and not apoptosis, over its entire effective concentration range. At each dose, both LDH and caspase activity were measured after incubation with PNC-28 after 24 h. For the points on the abscissa, two numbers are separated by a dash. The first number refers to the concentration of peptide; the second number refers to the particular peptide, e.g., "28" refers to PNC-28, while "29" refers to the negative control, PNC-29. Optical Density is shown as a function of treatment.

The results shown in FIGS. 4A-C were obtained using 25 μmol/ml PNC-28. As shown in FIG. 4D, the same results were obtained with all doses of compound that were used over the 20-75 μmol/ml range, i.e., early release of LDH (necrosis indicating) but only background levels of caspase (apoptosis indicating), suggesting that tumor cell necrosis is induced at all concentrations of PNC-28 and that this mechanism of induction of cell death is not dependent on PNC-28 concentration. As is shown on FIG. 4D, at 25 umol/ml PNC-28, caspase was approximately 0.03, while LDH was approximately 0.235 OD; at 50 umol/ml PNC-28, caspase was approximately 0.02, while LDH was approximately 0.44 OD; at 75 umol/ml PNC-28, caspase was approximately 0.015, while LDH was approximately 0.35 OD; and at 75 umol/ml PNC-29 (negative control), caspase was approximately 0.05, while LDH was approximately 0.01.

Transfection of MiaPaCa-2 Cells with a Plasmid that Encodes the p53 17-26 Sequence.

Results of Transfection of MiaPaCa-2 and BMRPA1 Cells.

After 2 hours post-transfection, cell counts were performed on slides using light microscopy and then counted the number of cells exhibiting green fluorescence from GFP (Green Fluorescent Protein). On this basis, it was found that between 30 and 45 percent of the cells expressed GFP as summarized in FIG. 9. The highest transfection rates were found for MiaPaCa-2 cells whether transfected with empty vector (EV) or p53 17-26-encoding vector (p53 17-26-V).

Morphological Examination of Transfected Cells, as Visualized by Inverted Light Microscopy: In the initial set of transfection experiments, cells were observed by light microscopy beginning 18 h post-transfection. MiaPaCa-2 cells transfected with p53 17-26-V were visibly hypertrophic, many showing membrane blebbing and some were necrotic. In contrast, BMRPA1 cells transfected in the same way as MiaPaCa-2 by either EV or p53 17-26-V showed little alteration in morphology. This observation was confirmed 90 h post-transfection, as the cells by this time point resumed their normal polygonal epithelial cell morphology, identical to that of untreated cells.

Cell Viability Post-Transfection.

Figure 5:
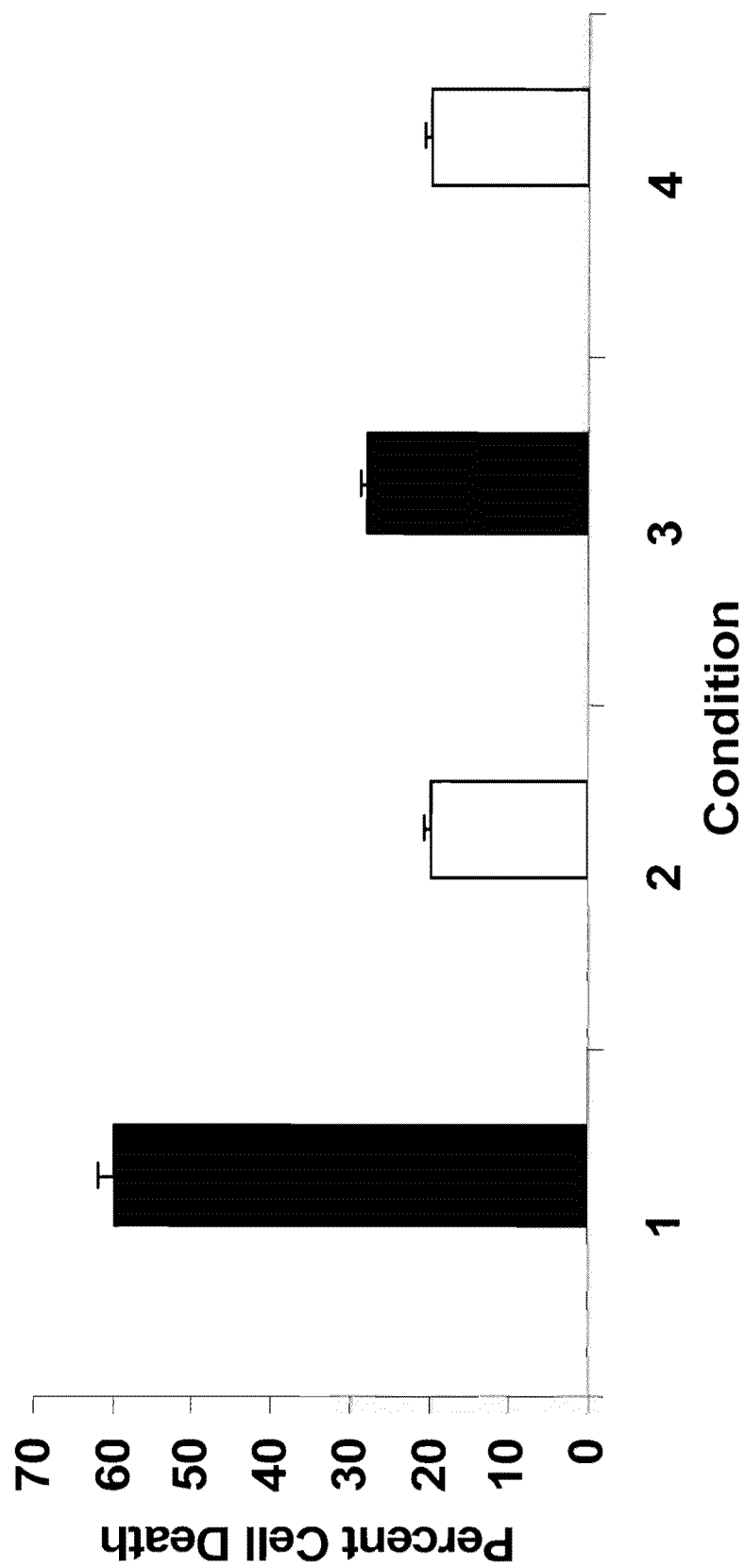
FIG. 5 is experimental data in the form of a chart which illustrates cell death (number of dead cells divided by total cell count) as measured by trypan blue dye exclusion in MiaPaCa-2 and BMRPA1 cells transfected with either p53 17-26-V or control p53 17-26-scrm-V plasmid, 48 h post-transfection. Condition 1: MiaPaCa-2 cells transfected with p53 17-26-V (black); condition 2: Mia-PaCa-2 cells transfected with p53 17-26-scrm-V (white); condition 3: BMRPA1 cells transfected with p53 17-26-V (black); condition 4, BMRPA1 cells transfected with p53 17-26-scrm-V (white).

FIG. 5 shows the effect of transfection of the plasmid p53 17-26-V encoding the p53 17-26 peptide on cell viability for MiaPaCa-2 and untransformed BMRPA1 cells. As can be seen in this FIG. 5, within 48 h, transfection of this plasmid induces 60 percent cell death (condition 1) while transfection of p53 17-26-scrm-V control plasmid results in a much lower level of cell death, i.e., 20 percent as shown in condition 2. This is a baseline level since this is the level of cell death observed for untransformed BMRPA1 cells transfected with the same control vector, condition 4. In condition 3 of this FIG. 5, it can be seen that expressed p53 17-26 peptide has a much less pronounced effect on BMRPA1 cells, resulting in the same baseline level of cell death seen in control plasmid-transfected BMRPA1 cells (condition 4). Thus, expression of the compound induces cell death in cancer, but not in untransformed, cells.

Effects of the p53 17-26 Peptide on MiaPaCa-2 Cells.

Figure 6:
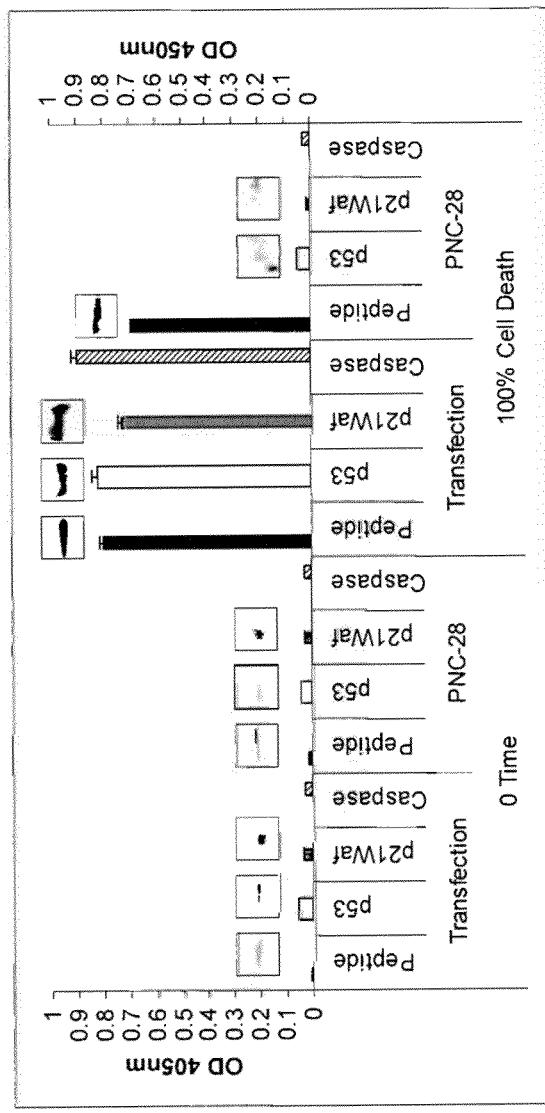
FIG. 6 is experimental data which shows the effects of expression of the p53 17-26 peptide, following transfection of its expression vector into MiaPaCa-2 cells, on expression of p53 and waf$^{p21}$, a cell cycle inhibitor protein induced by activated wild-type p53, as a function of time, measured by immunoblotting and on caspase activity. Peptide expression in cells was measured by blotting for the peptide with the anti-p53 monoclonal antibody DO-1 that recognizes the p53 17-26 sequence expressed by the plasmid. For comparison, the effects of incubating PNC-28 with MIA-PaCa-2 cells on induction of these proteins and on caspase activity are also shown. Intracellular PNC-28 level was determined using the same DO-1 antibody. The left ordinate shows the absorbance results for the caspase activity assay while the right ordinate shows the band intensity for each Western blot; the actual immunoblots are shown above each bar graph for the two proteins, p53, waf$^{p21}$ and each peptide (p53 17-26 and PNC-28). The left side of the figure shows the results for 0 time, after Mia-PaCa-2 cells were transfected with the plasmid (labeled as "transfection" in the figure) and immediately after PNC-28 was added to the incubation medium (labeled in the figure as "PNC-28."). The right side of the figure shows the results after close to 100 percent of the cells were killed by the plasmid-expressed peptide (labeled in the figure as "transfection") and by PNC-28 (labeled in the figure as "PNC-28"). Actin controls were the same for all four conditions (not shown).

MiaPaCa-2 cells expressing GFP that had been transfected with EV or p53 17-26-V were lysed and blotted for p53, waf$^{p21}$, a protein that is induced by a p53-dependent pathway, and the p53 17-26 peptide itself. In these experiments, the DO-1 anti-p53 antibody that recognizes a determinant that contains residues 17-26 of p53 was used (2). In addition, caspase activity in these cells was measured. For comparison, the same set of experiments was performed on Mia-PaCa-2 cells treated with 75 μmol/ml of PNC-28. As can be seen in FIG. 6, at 0 time (left side of FIG. 6, labeled "0 time") after transfection or incubation with PNC-28, peptide, p53, waf$^{p21}$ and caspase activity are all expressed at baseline levels. At times when cell death was near 100 percent at 96 hr for transfected cells, 48 hr for PNC-28-treated cells, peptide levels were found to be high in both transfected and PNC-28-treated cells (FIG. 6, right side, labeled "100% cell death"). However, in the transfected cells, it can be seen that there are elevated levels of p53, waf$^{p21}$ and caspase activity (labeled "transfection" on the right side of the figure) that are not observed in the PNC-28-treated cells (labeled "PNC-28" on the right side of the figure). For controls, actin was blotted for and it was found that the levels were the same for all four conditions in FIG. 6 (not shown). These results suggest that the p53 17-26 peptide induces increased intracellular expression of p53 protein with consequent apoptosis of MiaPaCa-2 cells, as evidenced by the concomitant increased expression of waf$^{p21}$ that does not occur in cells treated with PNC-28. Along the right axis, luminescence intensity is measured at 405 NM. Along the left axis, 450 NM measures the band intensity of the Western Blot. Interestingly, when lysates from untransformed BMRPA1 cells transfected either with EV or with p53 17-26-V were blotted, only low levels of expression of p53 were found. In addition, only a low level of expression of p53 17-26 peptide in p53 17-26-V-transfected cells was found (results not shown). Since GFP was expressed at high levels in these cells, it appears that expressed peptide is unstable in these untransformed cells.

Expressed p53 17-26 Peptide Induces Apoptosis, not Necrosis, of MiaPaCa-2 Cells.

Figure 7:
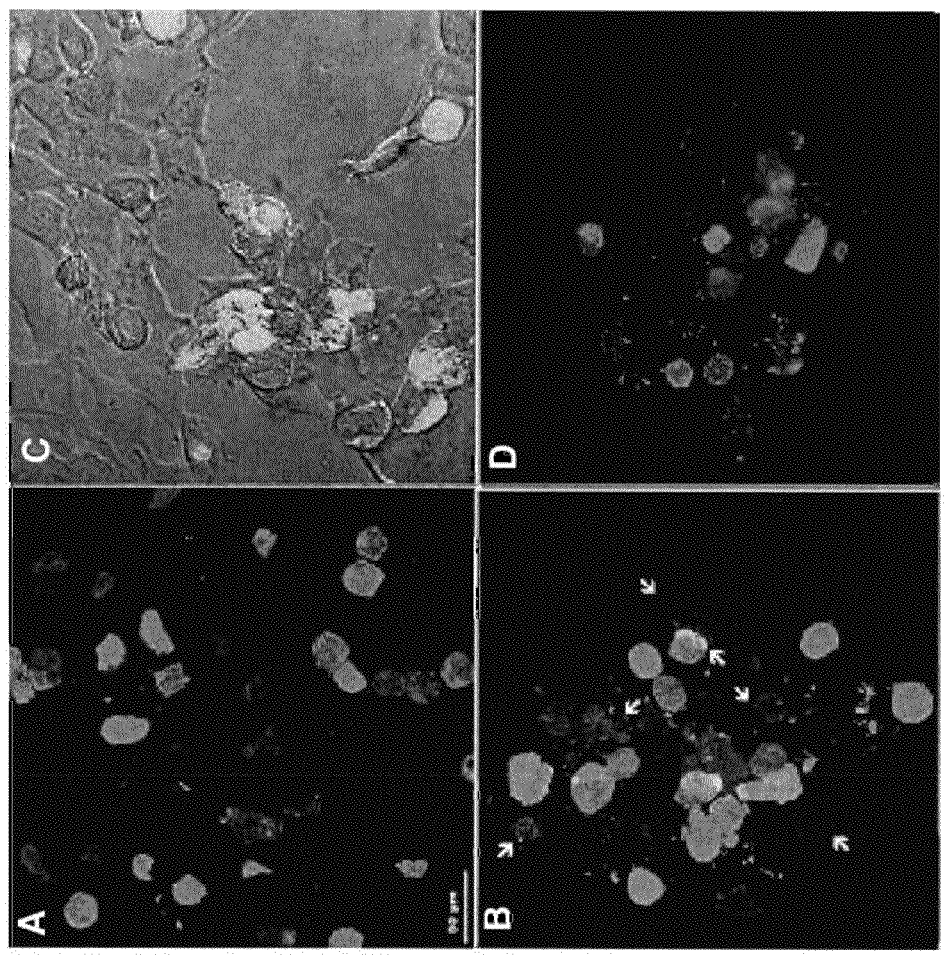
FIG. 7 is experimental data which illustrates that transfection of p53 17-26 vector induces apoptosis in MiaPaCa-2 but not BRMPA1 cells. Confocal microscopy demonstrating green fluorescence following transfection of control vectors into MiaPaCa-2 and BMRPA1 cells (Panels A and C) Annexin V binding to phosphatidyl serine (red staining) detected in p53 17-26-V-treated MiaPaCa-2 cells (Panel B) but not in 17-26-V-treated BMRPA1 cells (D).

Since expression of p53 and waf$^{p21}$ was elevated in cells transfected with p53 17-26-V to much higher levels than in cells transfected with control vector, it was concluded that the peptide was inducing apoptosis in contrast to its counterpart PNC-28 peptide as discussed above. Further confirmation of peptide-induced apoptosis was sought. In the early stages of apoptosis, phosphatidyl serine (PS), normally present in the inner leaflet of the bilayer membrane of intact cells, is found on the external plasma membrane of cells undergoing apoptosis Annexin V binds PS and can be located by a probe that carries the red fluorescent TRITC probe. Consequently, cells that had been transfected approx 48 h earlier were processed for staining with Annexin V-biotin followed by streptavidin-TRITC. FIG. 7 shows the confocal microscopic results for MiaPaCa-2 cells transfected with control vector (upper left), showing green fluorescent cells with no red staining, and cells transfected with p53 17-26-V that show green fluorescent cells with strong red staining for PS. On the right side of the figure are the results for BMRPA1 control cells that have been transfected with control vector (upper right) or p53 17-26-V (lower right). As can be seen in FIG. 7, neither panel is positive for PS in the normal control cells. As discussed above, expression of p53 17-26 peptide is low in this cell line, possibly causing the absence of signs of apoptosis. Thus the p53 17-26 peptide induces apoptosis in the cancer cell line only.

Caspase and LDH in Transfected MiaPaCa-2 Cells.

Figure 8A:
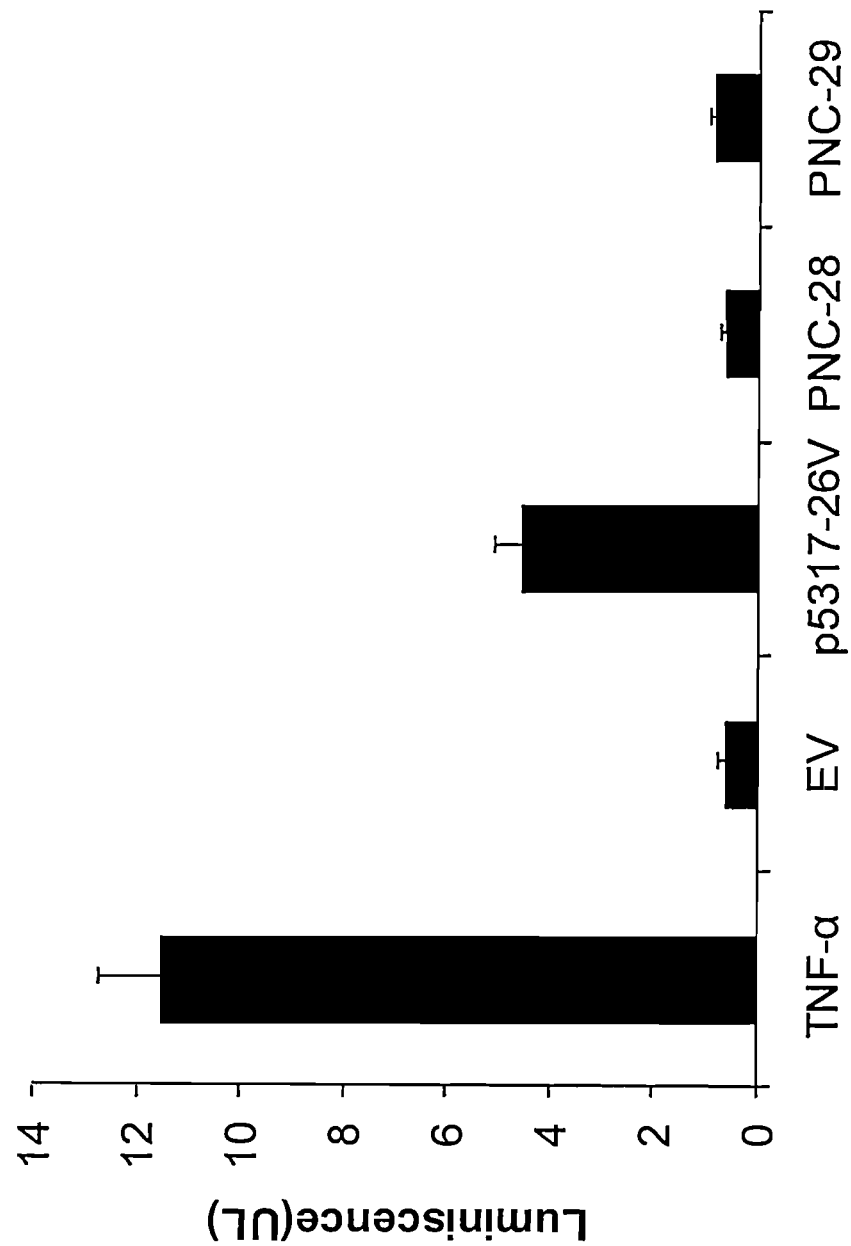
FIG. 8A is a chart of experimental data which illustrates that p53 17-26 induces cellular death by apoptosis. Caspase 3, 7 activity recorded (luminescence as labeled on the ordinate) for MiaPaCa-2 cells transfected with p53 17-26-V (condition 3), empty vector (condition 2), PNC-28 (condition 4), and PNC-29 (condition 5). Maximal caspase release is shown after treatment with TNF-α condition 1).
Figure 8B:
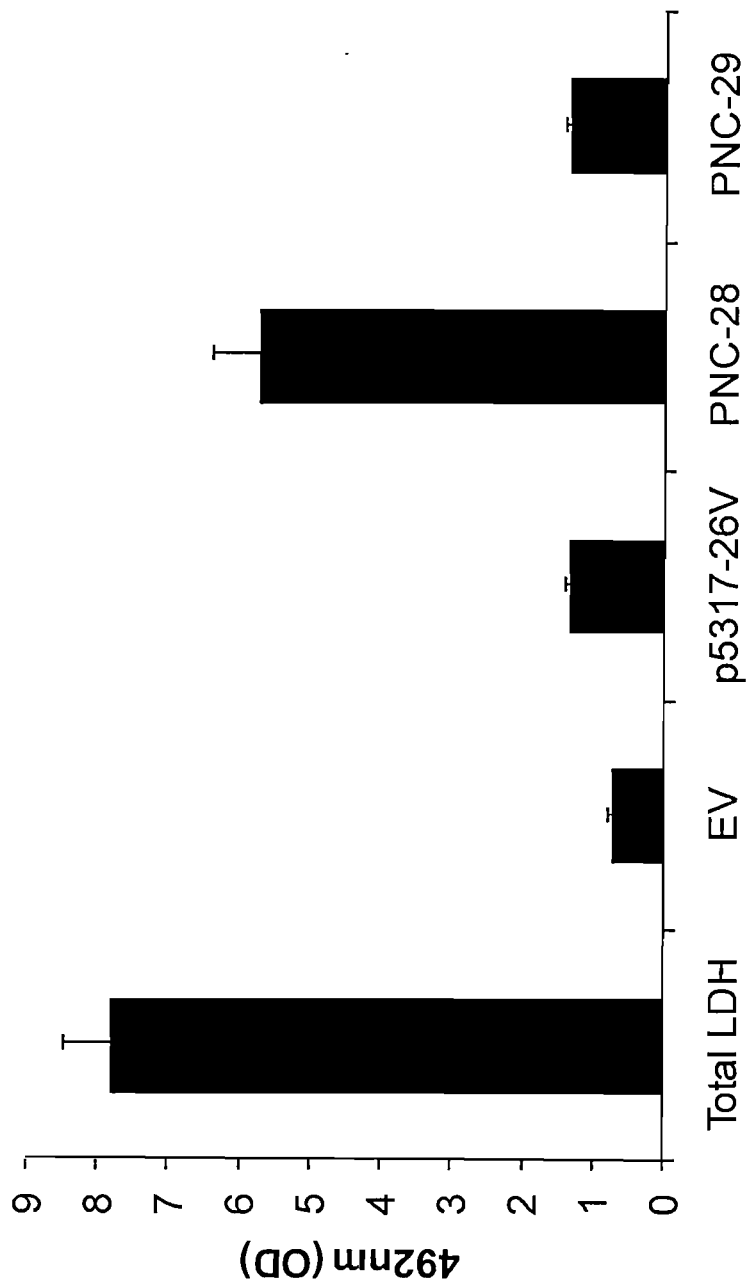
FIG. 8B is a chart of experimental data which illustrates that p53 17-26 induced cell death does not cause necrosis. LDH activity recorded for MiaPaCa-2 cells transfected with p53 17-26-V (condition 3), empty vector (condition 2), PNC-28 (condition 4), and PNC-29 (condition 5). Maximal LDH release is shown after treatment with lysis known buffer (condition 1).

To compare the results with those from MiaPaCa-2 cells treated with PNC-28 peptide (FIG. 4) p53 17-26-V-transfected cells were assayed for caspase and LDH release. As shown in FIG. 8A, condition 3, caspase expression is over four-fold higher in these treated cells than in untreated cells (condition 2) and has the same fold-increase over that in cells treated with PNC-28 and control PNC-29. In contrast, as shown in FIG. 8B, LDH release from these transfected cells (condition 3) is at the baseline level found for untreated cells (condition 2) and is about five-fold lower than release from cells treated with PNC-28 (condition 4). Thus, presence of the MRPin PNC-28 results in a change in the mechanism of action of the p53 17-26 peptide; without MRP, the peptide induces apoptosis, while, with MRP on its carboxyl terminal end, the peptide induces tumor cell necrosis.

Prior Evidence that the MRP in PNC-27 and PNC-28 Is Required for Induction of Tumor Cell Necrosis.

The purpose of this study was to define the role of the MRP in PNC-28 in inducing tumor cell necrosis. In previous studies with this MRP and its compound, PNC-27, it was found that both PNC-27 and PNC-28 induced tumor cell necrosis, not apoptosis, and caused necrosis even in cancer cells in which p53 protein was absent (1-3). These findings suggested that both PNC-27 and PNC-28 exerted their effects independently of p53 activation. They contrasted with the results of studies in which similar p53 sequences, were attached to MRP on their amino terminal ends, and induced p53-dependent tumor cell apoptosis, not necrosis (7-11). This results from the binding of these peptides to HDM-2 in place of the p53 protein; these peptides are not themselves ubiquitinated since the sites for p53 ubiquitination lie outside this domain (16).

Further evidence that the presence of the MRP on the carboxyl terminal end of PNC-27 and 28 is essential for its induction of tumor cell necrosis is the three-dimensional structure of PNC-27. PNC-27 was found to have a highly amphipathic alpha-helix-loop-alpha-helix structure that is found in membrane-active peptides (4). Disruption of this structure, as may occur by placement of the MRP on the amino terminal end of the compound, would be expected to change the activity of the compound. It was found that the p53 17-26 peptide containing the MRP on its amino terminus, called reverse or r-PNC-28, has much lower activity in cell killing than does PNC-28 itself (M. Kanovsky, J. Michl and M. R. Pincus, unpublished observations). These findings support the conclusion that the MRP is critical to the activity of the compound but leaves open the question as to whether the "naked" p53 peptide itself can induce necrosis or apoptosis of cancer cells.

Cells Transfected with pTracer-SV40 Plasmid Encoding p53 17-26 "Naked" Peptide Express this Peptide.

To define the role of the MRP definitively, it was sought to determine the effects of the p53 17-26 peptide itself on tumor cell growth, i.e., whether even without the MRP, it could induce tumor cell necrosis. To accomplish this goal, the p53 peptide was introduced into MiaPaCa-2 cells via transfection using the pTracer-SV40 plasmid that constitutively expressed this peptide. Then, the expression of markers for apoptosis and necrosis in the transfected cells and compared the levels of these markers with those found in MiaPaCa-2 cells treated with PNC-28 was determined.

As can be seen in FIG. 9, transfection efficiencies were relatively high. MiaPaCa-2 cells transfected with the p53 peptide-expressing plasmid expressed high levels of the p53 peptide and expressed high levels of GFP as revealed by Western blots over this time period. By 90 hours, when at least two-thirds of the cells were killed (FIG. 7), peptide expression decreased to barely detectable levels while GFP levels also decreased significantly (FIG. 6). This phenomenon may have been caused by cell death and release of proteases causing peptide degradation. On the other hand, BMRPA1 cells transfected with the same peptide-encoding plasmid expressed much lower levels of this peptide. Since these cells expressed high levels of GFP, which is expressed under the same promoter, it is not likely that p53 peptide was not also being synthesized in these cells. One possible explanation for this observation is the status of HDM-2. Recently, it was found by the present inventors that this protein is expressed at barely detectable levels in untransformed cells, including BMRPA1 cells, but is expressed at high levels in transformed cells. If binding of the small p53 decapeptide to HDM-2 blocks its degradation in cells, absence of HDM-2 may make the peptide susceptible to intracellular proteases resulting in its degradation.

The p53 17-26 Peptide Induces Apoptosis of Cancer Cells.

As summarized in FIG. 6, expression of the p53 17-26 peptide in MiaPaCa-2 cells induces increasing expression of p53 with concomitant increasing expression of $waf^{p21}$ over a time period in which cell death increases. These results are compatible with binding of the peptide to hdm-2, blocking the binding of p53 to this protein, resulting in prolongation of the half-life of p53. This would result in its increased expression in MiaPaCa-2 cells, allowing it to cause apoptosis, explaining the increasingly elevated levels of $waf^{p21}$. As shown in FIG. 8A, caspase, a marker for p53-dependent apoptosis, is elevated to almost five times the background level (condition 2) in p53 17-26 peptide-expressing MiaPaCa-2 cells (condition 3). Likewise, it is elevated above background in cells incubated with PNC-28 (condition 4). Also, in virtually all MiaPaCa-2 cells treated with p53 17-26 peptide-expressing cells, there was strong expression of annexin-V-binding phosphatidyl serine in the membranes of transfected MiaPaCa-2 cells, a known early phenomenon in apoptosis (15), but not in MiaPaCa-2 cells transfected with empty vector (FIG. 7). These results suggest that the naked p53 17-26 peptide causes cancer cell death by inducing apoptosis. Furthermore, the p53 peptide-expressing MiaPaCa-2 cells do not release LDH in 24 h (condition 3, FIG. 8B) as would be expected if the peptide induced tumor cell necrosis. In contrast, treatment of Mia-PaCa-2 cells with PNC-28 resulted in high levels of LDH (condition 2, FIG. 4A and condition 4 in FIG. 8B) over this time course that began as early as several minutes after treatment, confirming that the peptide induces tumor cell necrosis and not apoptosis. This effect is independent of the concentration of PNC-28, suggesting that its mechanism of action does not change in a concentration-related manner. This finding, that expression of the p53 17-26 peptide in a cancer cell line induces apoptosis, is in agreement with the results of prior studies that showed that similar peptides from the HDM-2 binding domain of p53 likewise induce apoptosis (7-12).

Overall, experimental results set forth herein strongly suggest that the p53 17-26 peptide induces tumor cell apoptosis and not necrosis. On the other hand, presence of the MRP to the carboxyl terminal end of the p53 17-26 peptide plays a critical role in changing the mechanism of cell killing of this peptide from apoptosis to tumor cell necrosis.

The p53 17-26 Peptide Induces Apoptosis in Tumor but not Normal Cells.

As shown in FIG. 5, transfection of empty vector in Mia-PaCa-2 cells causes a low level of cell death. However, as shown in FIG. 7, transfection of empty vector into MiaPaCa-2 cells causes no exposure of phosphatidyl serine as revealed by absence of annexin V binding suggesting that the transfection does not induce apoptosis. On the other hand, transfection of the vector inducing expression of the p53 17-26 sequence into these cells induces higher rates of cell death (FIG. 5). In all of these cells, as shown in FIG. 7, there is strong annexin binding suggesting that these cells are all undergoing apoptosis.

In contrast, transfection of the p53 peptide-expressing vector into untransformed BMRPA1 cells does not result in an increase in cell death over the background (FIG. 7). Furthermore, neither transfection of empty vector or of p53 peptide-expressing vector results in any exposure of annexin-binding phosphatidyl serine (FIG. 8). These findings may be due at least partly to the low level of expression of the p53 17-26 peptide. Nonetheless, the p53 peptide-encoding plasmid does not induce apoptosis in untransformed BMRPA1 cells. Thus, like PNC-27 and PNC-28, the p53 17-26 peptide appears to be selective for killing cancer but not untransformed cells.

In summary, the MRP on the carboxyl terminal end of PNC-28 causes it to induce tumor cell necrosis. Removal of the MRP from the p53 17-26 peptide in cancer cells results likewise in cytotoxicity to these cells except by apoptosis of the tumor cells. Thus presence of the MRP on the carboxyl terminal end of p53 peptide results in a fundamental change in the mechanism of action of the compound in causing tumor cell death. Like the full peptide, PNC-28, the naked p53 17-26 peptide appears to be selective to inducing apoptosis of cancer cells but not of untransformed cells. This may be due in part to low levels of expression of the peptide in untransformed cells that express low levels of HDM-2 that may shield expressed peptide from protease degradation. This finding implies that introduction of the naked peptide into cells can induce tumor cell apoptosis while leaving normal cells unaffected.

These results underscore the importance of elucidating the p53-hdm-2 interaction in the cancer cell, whereby it is possible to gain a better understanding of the manner of which this complex potentiates a possible cross-talk between necrotic and apoptotic pathways that may lead to novel approaches for directed therapy. As a result, such with HDM-2 targeting component(s) and MRP(s) therapeutics may deliver selective cytotoxic small molecules to cancer cells targeting pathways inducing necrosis, apoptosis or both.

A method of selectively necrosing cells is provided. The method includes the steps of providing a plurality cells, including at least one cancer cell and at least one non-cancerous cell; and administering to the cells a compound, including an HDM-2 targeting component and a cytotoxic component, said cytotoxic component attached to said HDM-2 targeting component, wherein said compound comprises a membrane-active form. The cytotoxic component may desirably be, for example, a membrane resident peptide (MRP), a toxin, a drug, a radionuclide, a whole antibody, an antibody fragment, and combinations thereof. The HDM-2 targeting component may be, for example, a small molecule, a peptide, a protein, a glycoprotein, a whole antibody, an antibody fragment, and combinations thereof.

One or more of the methods may optionally include the step of observing, in a cell medium, a level of LDH. A level of LDH may be an amount of LDH measured as omitted from a number of cells. LDH is known necrosis indicator, thus, the presence of LDH in the cell medium of cells treated with the compound of the present method indicates that at least some of the cells have undergone necrosis, cell death. Necrosis may similarly be observed in a sample of cells by microscopically inspecting the cells to determine whether the cell membranes are intact or have transmembrane pore formation therein/thereon.

Though the compound of the present method selectively necroses cancer cells, the compound has no observable effect on non-cancerous cells. Thus, the method may further comprise the step of observing for a non-response in a non-cancerous cell. The cells may be observed for pore formation, cell breakdown, and the like. However, observation and/or analysis of the non-cancerous cells will yield no effect on the non-cancerous cells. Similarly, this no effect may be referred to as a non-response by the non-cancerous cells to the cancer treatment (compound) administered. As such, the present method results in necrosis of cancer cells, while non-cancerous cells are unaffected.

A method of causing membranolysis in at least one cancer cell is provided. The method of causing membranolysis in at least one cancer cell further includes administering to at least one cancer cell a compound comprising an HDM-2 targeting component and a pore forming component attached to said HDM-2 targeting component, wherein said administering step results in at least one transmembrane pore in a cancer cell membrane. The pore forming component may include, for example, any chemical moiety with a pore forming character when put into association with a cell membrane, desirably, a cancer cell membrane. The pore forming component may include, for example, a membrane resident peptide (MRP).

Causing membranolysis in cancer cells is a desirable basis for cancer treatments. The present method may be employed to more readily understand the dosing effectiveness of the cancer treatment and/or compound. Thus, administration of multiple dosages may be completed in order to more readily understand the upper and lower limits of effectiveness, if any. Further, the effectiveness of various treatment plans, repeating administration, may be studied utilizing this method. Also, various types of cancer cells and/or pre-cancerous cells (atypical cells) may be studied to analyze and determine varying levels of aggressiveness, progression, treatability, and/or responsiveness to dosages of the compound of the present method.

The method of causing membranolysis in at least one cancer cell may further include observing membranolysis in the cancer cell by: detecting an LDH amount, performing electron microscopy, observing cell morphology, and combinations thereof. By observing membranolysis, the effectiveness of various dosages and, potentially, the effectiveness combination therapies, may be better understood. The observation of membranolysis is linked to necrosis in the cancer cells, as the structural integrity of the cell is no longer maintained once transmembrane pores trigger membranolysis. However, varying degrees of necrosis may be observed. This may be due, in part, to the natural breakdown of the compound within a sample or a subject. Further, this may be linked to dosage, strength of the cancer cells, or duration of treatment.

A method of treating cancer in a subject in need thereof is provided. The method includes administering to the subject in need thereof a therapeutically effective amount of a compound having an HDM-2 targeting component and a membrane resident peptide (MRP), said HDM-2 targeting component and said MRP having a membrane-active form. After the administration step, optionally, the method may include determining whether a plurality of cancerous cells have undergone membranolysis.

The cytotoxic component may include, for example, a membrane resident peptide, a toxin, a drug, a radionuclide, a whole antibody, an antibody fragment, and combinations thereof. The HDM-2 targeting component is selected from the group consisting of: a small molecule, a peptide, a protein, a glycoprotein, a whole antibody, an antibody fragment, and combinations thereof.

A method of screening cancer treatments is provided. The method includes providing a plurality of cancerous cells; each of said cells having HDM-2 in said cellular membranes; administering a candidate cancer treatment to the plurality of cancer cells; and measuring the level of LDH present in a cellular medium. LDH is a known necrosis factor, thus, the measurement of a level or amount of LDH present after administering a candidate cancer treatment to the cancer cells with detect whether the cancer treatment was successful in causing cell death to cancer cells.

Optionally, the candidate cancer treatment may be screened to determine whether the candidate cancer treatment has membrane active conformation. The membrane active conformation may refer to the desired shape of the candidate cancer treatment in solution. The conformation may be directly linked to the candidate cancer treatment's ability to colocalize with HDM-2 in the cancer cell membrane and be retained within the cancer cell membrane, causing the formation of pores therein. Desirably, candidate cancer treatments may have a three dimensional shape or conformation in an alpha-helix-loop-alpha-helix. This is the three-dimensional shape that has been determined by the present inventors for the PNC-27 and PNC-28 peptide-based compositions. The alpha-helix-loop-helix conformation allows the composition to advantageously interact with the cancer cell membrane.

Optionally, the candidate cancer treatment may be screened to determine the candidate cancer treatment includes an HDM-2 targeting component. To determine this, it is possible to analyze the HDM-2 targeting component to determine whether it has any affinity and or binding capability to HDM-2 in cancer cell membranes.

Optionally, the method may further include the step of observing the cancer cell membranes for an area of pore formation. Pore formation is the mechanism by which membranolysis is caused, which results in cancer cell death. Pore formation may be microscopically observed. Also, various assays may be completed, measuring known necrotic factors, including, for example, LDH.

A candidate cancer treatment which may be found to have a membrane active form, cause membranolysis to cancer cells, have a similar conformation to PNC-27 and/or PNC-28, and have an HDM-2 binding affinity may be termed a material with anti-cancer "activity". Use of the term "activity" with respect to a cancer treatment with reference to the embodiments of the present invention refers to an ability to induce a desirable effect upon in vitro, ex vivo, or in vivo administration of the compound. Desirable effects include preventing or reducing the likelihood (increasing the likelihood or causing) one or more of the following events: binding to HDM-2 in cancer cells, insertion into the cancer cells' plasma membrane, assembly and pore foundation, transport across the cancer cell membrane, causing membranolysis. Materials with anti-cancer "activity" may be flagged for further testing, review, and consideration as viable cancer treatments.

Identifying drug candidates from cancer candidate treatments flagged as having "activity", typically involves multiple phases. During the early stages, compounds, preferably large libraries of compounds are screened or tested in vitro for binding to and/or biological activity at the cancer cell membrane (with HDM-2 and/or a membrane resident component characteristic). The compounds that exhibit activity ("active compounds" or "hits") from this initial screening process are then tested through a series of other in vitro and in vivo tests to further characterize the anti-cancer normal, non-cancerous tissue and organ protective activity of the compounds.

The in vivo tests at this phase may include tests in non-human mammals such as those mentioned above. If a compound meets the standards for continued development as a drug following in vitro and in vivo tests, the compound is typically selected for testing in humans.

A progressively smaller number of test compounds at each stage are selected for testing in the next stage. The series of tests eventually leads to one or a few drug candidates being selected to proceed to testing in human clinical trials. The human clinical trials may include studies in a human suffering from a medical condition that can be treated or prevented by reducing cancer cells (inducing cancer cell necrosis).

A method of selectively necrosing cancer cells is provided. The method includes providing a plurality of cells, including at least one cancer cell and at least one non-cancerous cell; and contacting the plurality of cells with an HDM-2 targeting compound which includes a membrane resident peptide (MRP), wherein the HDM-2 targeting compound colocalizes to HDM-2 present in at least one cancer cell membrane, binding to a cell membrane of the at least one cancer cell and adopting a membrane-resident conformation within said cancer cell membrane.

The adoption of a membrane-resident conformation may further include forming a pore in said cancer cell membrane. Optionally, the method may include observing necrosis in the plurality of cancer cells, while observing necrosis was previously discussed. Similarly, the method may include the step of optionally observing a non-result in the non-cancerous cells, which is indicative of non-targeting of said non-cancerous cells by the method and its related compound.

A method of identifying cancer cells is provided. The method of identifying cancer cells includes providing a plurality of cells, wherein at least one of said cells is a candidate cancer cell; and administering to the plurality of cells an HDM-2 recognition agent.

Candidate cancer cells, as used herein, may generally refer to cells, cellular samples, or tissues which may include cancer calls, pre-cancerous cells, and non-cancerous cells. The method of the present invention may be used to determine which of the cells, if any, within the candidate cancer cells are cancerous. The plurality of candidate cancer cells may be optionally observed to determine whether the HDM-2 recognition agent colocalizes with at least one cell membrane. Colocalization may result in the HDM-2 recognition molecule being bound to or transported through the cell membrane, depending on the form of the HDM-2 recognition agent. If the HDM-2 recognition agent takes on the form of PNC-27, or a non-peptide component with an MRP attached thereto, the HDM-2 recognition agent will be taken into the cell membrane of cancer cells, in a membrane active form. This is indicative of the recognition agent's tendency to be bound to HDM-2 in a cancer cell.

In order to better observe and determine which candidate cancer cells, if any, are cancerous, it is possible to optionally tag the HDM-2 recognition agent with an observation aid. The observation aid may be attached to the HDM-2 recognition agent such that the observation aid follows the HDM-2 recognition agent and does not interfere with any colocalization to HDM-2 in the cancer cell membranes. The observation aid may include one or more materials, as may be desired. The observation aid may be, for example, a dye, a fluorescing agent, a radiopaque material, a radioactive isotope, and combinations thereof. One useful observation aid may include, for example, horseradish radish peroxidase.

Identifying at least one cancer cell may refer to identifying that the HDM-2 recognition agent has colocalized with, bound to, or otherwise affiliated with the surface of a cellular membrane containing HDM-2. This may be based on the premise that HDM-2 is contained in cancer cells at roughly five times greater presence than in non-cancerous cells.

Once the HDM-2 recognition agent has tagged or affiliated to cancer cell membranes present out of the total candidate cancer cells (or surrounding non-cancerous tissue), it is possible to quantify and qualify the size, shape, progression, and general nature of a plurality of cancer cells. Thus, a plurality of cancer cells may be mapped or plotted with respect to the surrounding frame of reference (in a subject, the surrounding anatomy and/or tissues), in order to better understand the placement and size of the cancer cells (cancerous tissue). The observation aids, including, for example, dyes, fluorescing agents, radiopaque materials, and the like, may aid in visualizing the HDM-2 recognition agent within a sample that may have a large amount of cells present. Thus, once the HDM-2 recognition agent is administered to cells, various known visualization techniques, including filtered scopes to detect light at certain wavelengths of the electromagnetic spectrum, x-ray, catscan, and the like may be employed in order to better see and understand the plurality of cancerous cells. Thus, the map of the cancer cells may be useful in diagnosing types of cancer, treatments for cancer, surgical removal thereof, observing the progression, monitoring for relapse of cancer, and/or the responsiveness to treatments.

The compounds, agents, and or materials used in conjunction with one or more of the methods of the present invention may refer to PNC-27, PNC-28, or combinations thereof, as discussed herein. Further, it should be readily understood that non-peptide materials which may desirably have an HDM-2 affinity or binding site may be used in conjunction with the MRP. Hybrid materials containing peptide and non-peptide components, along with wholly non-peptide materials may be used with one or more of the methods of the present invention. The synthesis of one or more of the compounds may be subsequently followed by purification, as is commonly done in the art. The compounds synthesized are preferably in purified form to be used as the compound and with the methods of the present invention. Thus, the present invention contemplates the use of peptide as well as non-peptide materials, and combinations thereof, to cause selective necrosis to cancer cells, in accordance with the present invention.

One or more of the methods referenced herein may optionally include a reiteration or repeated administration step. That is, after the administration step, it is possible to determine whether a plurality of subsequent cancer cells exist and remain intact. If so, it is possible to complete one or more of the method steps for each of the methods previously discussed, including the administration of the compound, HDM-2 recognition agent, and the like.

The compounds, agents, and materials used in conjunction with one or more of the aforementioned methods are desirably in a purified form. Purified form, as used herein, generally refers to material which has been isolated under certain desirable conditions that reduce or eliminate unrelated materials, i.e. contaminants. Substantially free from contaminants generally refers to free from contaminants within analytical testing and administration of the material. Preferably, purified material is substantially free of contaminants is at least 50% pure, more preferably, at least 90% pure, and more preferably still at least 99% pure. Purity can be evaluated by conventional means, e.g. chromatography, gel electrophoresis, immunoassay, composition analysis, biological assay, NMR, and other methods known in the art.

At least one cancer cell, as used herein, may similarly refer to a plurality of cancer cells. A plurality of cells may include, a sample of cells, a tissue sample, a tumor, and/or even a subject having cancer. At least one cell may refer to one cell, a plurality of cells, a sample of cells, a tissue sample, and/or even a subject. A plurality of cells including at least one cancer cell and at least one non-cancerous cell may refer to a mixture of cells in a sample, an area of tissue including both cancerous and non-cancerous tissues, and or a subject diagnosed with cancer.

The term "subject", as used herein may refer to a patient or patient population diagnosed with, or at risk of developing one or more forms of cancer. Also, as used herein, a subject may refer to a living animal, including mammals, which may be given cancer through transplantation or xenotransplanting which may be subsequently treated with the methods and compounds of the present invention or which have developed cancer and need veterinary treatment. Such subjects may include mammals, for example, laboratory animals, such as mice, rats, and other rodents; monkeys, baboons, and other primates, etc. They may also include household pets or other animals in need of treatments for cancer.

The terms "therapeutically effective dosage" and "effective amount" refer to an amount sufficient to kill one or more cancer cells. A therapeutic response may be any response that a user (e.g. a clinician will recognize) exhibits as an effective response to the therapy, including the foregoing symptoms and surrogate clinical markers. Thus, a therapeutic response will generally be an amelioration or inhibition of one or more symptoms of a disease or disorder, e.g. cancer.

Administering, as referred to by one or more of the methods of the present invention, may include contacting. The term "contacting" refers to directly or indirectly bringing the cell and the compound together in physical proximity. The contacting may be performed in vitro or in vivo. For example, the cell may be contacted with the compound by delivering the compound into the cell through known techniques, such as microinjection into the tumor directly, injecting the compound into the bloodstream of a mammal, and incubating the cell in a medium that includes the compound.

Any method known to those in the art for contacting a cell, organ or tissue with a compound may be employed. Suitable methods include in vitro, ex vivo, or in vivo methods. In vitro methods typically include cultured samples. For example, a cell can be placed in a reservoir (e.g., tissue culture dish), and incubated with a compound under appropriate conditions suitable for inducing necrosis in cancer cells. Suitable incubation conditions can be readily determined by those skilled in the art.

Ex vivo methods typically include cells, organs or tissues removed from a mammal, such as a human. The cells, organs or tissues can, for example, be incubated with the compound under appropriate conditions. The contacted cells, organs or tissues are normally returned to the donor, placed in a recipient, or stored for future use. Thus, the compound is generally in a pharmaceutically acceptable carrier.

In vivo methods are typically limited to the administration of a compound, such as those described above, to a mammal, preferably a human. The compounds useful in the methods of the present invention are administered to a mammal in an amount effective in necrosing cancer cells for treating cancer in a mammal. The effective amount is determined during pre-clinical trials and clinical trials by methods familiar to physicians and clinicians.

The compounds useful in the methods of the invention may also be administered to mammals by sustained release, as is known in the art. Sustained release administration is a method of drug delivery to achieve a certain level of the drug over a particular period of time. The level typically is measured by serum or plasma concentration.

The compounds of one or more of the aforementioned methods of the present invention may be administered to a human in an amount effective in achieving its purpose. The effective amount of the compound to be administered can be readily determined by those skilled in the art, for example, during pre-clinical trials and clinical trials, by methods familiar to physicians and clinicians. Typical daily doses include approximately 1 mg to 1000 mg.

An effective amount of a compound useful in the methods of the present invention, preferably in a pharmaceutical composition, may be administered to a mammal in need thereof by any of a number of well-known methods for administering pharmaceutical compounds. The compound may be administered systemically or locally.

Any formulation known in the art of pharmacy is suitable for administration of the compounds useful in the methods of the present invention. For oral administration, liquid or solid formulations may be used. Some examples of formulations include tablets, capsules, such as gelatin capsules, pills, troches, elixirs, suspensions, syrups, wafers, chewing gum and the like. The compounds can be mixed with a suitable pharmaceutical carrier (vehicle) or excipient as understood by practitioners in the art. Examples of carriers and excipients include starch, milk, sugar, certain types of clay, gelatin, lactic acid, stearic acid or salts thereof, including magnesium or calcium stearate, talc, vegetable fats or oils, gums and glycols.

Formulations of the compounds useful in the methods of the present inventions may utilize conventional diluents, carriers, or excipients etc., such as those known in the art to deliver the compounds. For example, the formulations may comprise one or more of the following: a stabilizer, a surfactant, preferably a nonionic surfactant, and optionally a salt and/or a buffering agent. The compound may be delivered in the form of an aqueous solution, or in a lyophilized form. Similarly, salts or buffering agents may be used with the compound.

The compounds of the present invention may be administered in therapeutically effective concentrations, to be provided to a subject in standard formulations, and may include any pharmaceutically acceptable additives, such as excipients, lubricants, diluents, flavorants, colorants, buffers, and disintegrants. Standard formulations are well known in the art. See, e.g. Remington's pharmaceutical Sciences, 20th edition, Mach Publishing Company, 2000. The formulation may be produced in useful dosage units for administration by any route that will permit the compound to contact the cancer cell membranes. Exemplary routes of administration include oral, parenteral, transmucosal, intranasal, insulfation, or transdermal routes. Parenteral routes include intravenous, intra-arterial, intramuscular, intradermal, subcutaneous, intraperitoneal, intraductal, intraventricular, intrathecal, and intracranial administrations.

The pharmaceutical forms suitable for injection include sterile aqueous solutions or dispersions and sterile powders for the extemporaneous preparation of sterile injectable solutions or dispersions. The ultimate solution form in all cases must be sterile and fluid. Typical carriers include a solvent or dispersion medium containing, e.g., water buffered aqueous solutions, i.e., biocompatible buffers, ethanol, polyols such as glycerol, propylene glycol, polyethylene glycol, suitable mixtures thereof, surfactants or vegetable oils. Sterilization may be accomplished utilizing any art-recognized technique, including but not limited to filtration or addition of antibacterial or antifungal agents.

The compounds of the present invention may be administered as a solid or liquid oral dosage form, e.g. tablet, capsule, or liquid preparation. The compounds may also be administered by injection, as a bolus injection or as a continuous infusion. The compounds may also be administered as a depot preparation, as by implantation or by intramuscular injection.

The compounds, agents, and materials referenced in the present invention may be in a "pharmaceutically acceptable carrier". A pharmaceutically acceptable carrier includes any and all solvents, dispersion media, coatings, antibacterial and antifungal agents, isotonic agents and the like. The use of such media and agents are well-known in the art. The phase 'pharmaceutically acceptable' refers to molecular entities and compositions that are physiologically tolerable and do not typically produce unwanted reactions when administered to a subject, particularly humans. Preferably, as used herein, the term "pharmaceutically acceptable" means approved by a regulatory agency of the federal or a state government or listed in the U.S. Pharmacopeia or other generally recognized pharmacopeia for use in animals, and more particularly, in humans. The term carrier refers to a diluent, adjuvant, excipient or vehicle with which the compounds may be administered to facilitate delivery. Such pharmaceutical carriers can be sterile liquids, such as water and oils, or organic compounds. Water or aqueous solution saline solutions, and aqueous dextrose and glycerol solutions are preferably employed as carriers, particularly as injectable solutions.

The synthetic peptides which may include the compounds, agents, and materials used with the present methods of the present invention may be synthesized by a number of known techniques. For example, the peptides may be prepared using the solid-phase technique initially described by Merrifield (1963) in J. Am. Chem. Soc. 85:2149-2154. Other peptide synthesis techniques may be found in M. Bodanszky et al. Peptide Synthesis, John Wiley and Sons, 2d Ed., (1976) and other references readily available to those skilled in the art. A summary of polypeptide synthesis techniques may be found in J. Stuart and J. S. Young, Solid Phase Peptide Synthesis, Pierce Chemical Company, Rockford, Ill., (1984). Peptides may also be synthesized by solid phase or solution methods as described in The Proteins, Vol. II, 3d Ed., Neurath, H. et al., Eds., pp. 105-237, Academic Press, New York, N.Y. (1976). Appropriate protective groups for use in different peptide syntheses are described in the texts listed above as well as in J. F. W. McOmie, Protective Groups in Organic Chemistry, Plenum Press, New York, N.Y. (1973). The peptides of the present invention may also be prepared by chemical or enzymatic cleavage from larger portions of the p53 protein or from the full length p53 protein. Likewise, membrane-resident sequences for use in the synthetic peptides of the present invention may be prepared by chemical or enzymatic cleavage from larger portions or the full length proteins from which such leader sequences are derived.

Additionally, the peptides of the present invention may also be prepared by recombinant DNA techniques. For most amino acids used to build proteins, more than one coding nucleotide triplet (codon) can code for a particular amino acid residue. This property of the genetic code is known as redundancy. Therefore, a number of different nucleotide sequences may code for a particular subject peptide selectively lethal to malignant and transformed mammalian cells. The present invention also contemplates a deoxyribonucleic acid (DNA) molecule that defines a gene coding for, i.e., capable of expressing a subject peptide or a chimeric peptide from which a peptide of the present invention may be enzymatically or chemically cleaved.

Thus, the embodiments of the present invention use the proposed mechanism of interaction between HDM-2 and the compounds of the present invention. By incorporating a peptide sequence that shares certain p53 aa residues into the compound, the inventors are promoting the compound to bind to HDM-2 in the cancer cell membrane. Further, by combining the HDM-2 targeting component with an MRP, as the compound is transported over the cancer cell membrane, the binding of the compound to the cell causes membranolysis of the cancer cell membrane. This, in turn results in cell death through necrosis. The inventors of the present invention have thus invented cancer treatments that kill cancer cells, even when mixed with healthy cells. The methods of the present invention may be used to selectively kill cancer cells, thus creating a pinpointed treatment in a cell sample, tissue sample, or even within a patient's body. The methods of the present invention thus target HDM-2 in the cancer cell membrane; rather than p53. Thus, the HDM-2 targeting treatments of the present invention are applicable to all cancer cells, including those that have no p53 present, or may have p53 in an inactive (mutated) form.

It should be readily understood and appreciated that each of the elements and features of the present invention discussed with one embodiment may be similarly employed with other embodiments disclosed herein, and this discussion is by no means deemed limiting to the various additional permutations that may be employed, for example, with the methods presented herein.

As the methods of treatment do not cause cell death of normal cells, these methods of treatment are focused on the cancer cells, irrespective of the mode of administration to the cell sample. Thus, these methods of treatment may be used for tumors or cancers that are widespread, inoperable, or otherwise not effectively treated with conventional means or combination therapies.

Examples

Materials and Methods

Peptides.

The following peptides were synthesized by solid phase methods and were purified to >95% purity (Biopeptides Corp, La Jolla, Calif.): PNC-27 containing residues 12-26 (PPLSQETFSDLWKLL) (SEQ ID NO: 8) from the hdm-2 binding domain of p53 and PNC-28 (ETFSDLWKLL) (SEQ ID NO: 32) containing residues 17-26 from the hdm-2 binding domain of p53, both attached on their carboxyl terminal ends to the transmembrane-penetrating sequence which is related to the reverseomer sequence of the antennapedia sequence, KKWKMRRNQFWVKVQRG (SEQ ID NO: 1), also called MRP; the control peptide PNC-26, containing only residues 12-26 of p53 and no MRP; the control peptide PNC-29, an unrelated peptide from cytochrome P450 (also called X13) (bold) attached to MRP (italics), whose sequence is MPFSTGKRIMLGEKKWKMRRNQFWVKVQRG (SEQ ID NO: 4); and PNC-7, a peptide from the ras-p21 protein containing ras-p21 residues 35-47 (TIEDSYRKQV-VID) (SEQ ID NO: 7) attached to the MRP having SEQ ID NO: 1 on its carboxyl terminal end. In addition, a fluorescent-labeled form of PNC-27 was synthesized, i.e., PNC-27 peptide conjugated to the fluorescent dye, fluorescein isothiocyanate (FITC) on its amino terminal end (Biopeptides Corp.).

Cells.

MiaPaCa-2 cells (human pancreatic cancer cells) were obtained from the American Type Culture Collection (ATCC) (Manassas, Va.) and were cultured in DMEM supplemented with 10 percent bovine fetal serum and penicillin/streptomycin [100 U/100 ug/ml] as recommended by the ATCC. BMRPA1 cells (untransformed rat pancreatic acinar cells) were cultured as described previously (1).

Methods

Preparation of Plasmids.

DNA encoding the human p53 amino acid residues 17-26 sequence, corresponding to the p53 sequence in PNC-28, was cloned into the mammalian pTracer-SV40 (green-fluorescent protein [GFP]-expressing) expression vector downstream to the SV40 promoter. This vector constitutively expresses a cloned gene (Invitrogen, Carlsbad, Calif.). Also included in the vector is another expression cassette which is linked in tandem to the SV40-p53 17-26-expressing unit. The second expression cassette contains a CMV promoter driving the expression of the GFP-Zeocin resistance gene fusion protein. The vector was used to transform TOP10F' chemically competent E. coli following the Hanahan Method of transformation (13), and plated on Zeocin-containing agar plates for overnight growth. Eight colonies were then used to inoculate cultures in Low Salt Luria Broth (1% bacterial tryptone, 0.5% yeast extract, 0.5% NaCl, and 25 m/ml Zeocin). Cultures were grown under constant shaking at 200 rpm for 16 h in a 37° C. incubator, and plasmids were then extracted using a Qiagen Spin Miniprep Kit.

The construct sense and anti-sense strands of the cDNA encoding the p53 17-26 sequence (Invitrogen, Carlsbad, Calif.) were synthesized. The sense strand sequence was 5'-AGTCGAATTCGCCACCATGGAAACATTTTCAGACCT-ATGGAAACTA TTTGAGCGGCCGCAGTC-3') (SEQ ID NO: 31). Underlined EcoRI and NotI sites are located in 5' and 3' ends of the cDNA, respectively. Start and stop codons are in italics. The p53 17-26 coding sequence is in bold letters. For maximum protein translation in transfected cell lines, the start codon was placed within a Kozak sequence, i.e., GCCACCATGG (SEQ ID NO: 30) (with ATG being the start codon), which is the optimal context for initiation of translation in vertebrate mRNA (13). The strands (250 nmol/ml) were annealed in annealing buffer by heating to 95° C., and then cooling to room temperature. The annealed double stranded p53 17-26-encoding cDNA was then digested with NotI and EcoRI simultaneously. A total of 20 ug of pTracer-SV40 was digested with 60 units of NotI and 60 units of EcoRI. Double-digested pTracer-SV40 and p53 17-26-encoding cDNA were then electrophoresed through 0.8% and 2.5% agarose gel, respectively. Gel bands containing DNA of appropriate size were excised, and DNA content was extracted using the NucleoTrap Gel Extraction kit (ClonTech, Mountain View, Calif.). Purified vector and cDNA were ligated with T4 ligase (12 hr, 4° C.) (New England Biolab, Ipswich, Mass.). Two ul of ligation reaction was then dispensed into a vial containing 50 ul One Shot TOP10F' competent E. coli (Invitrogen), and the reaction mixture was incubated on ice for 10 min, heat-shocked to 42° C. (30 sec) and incubated on ice for another 2 min. A total of 250 ul SOC medium (Invitrogen) was then added to the cells which were then shaken at 37° C. (1 hr). This transformation reaction was then diluted 1:100 or 1:10 using SOC medium. A total of 50 ul of each was spread on LB plates containing 12.5 µmol/ml ampicillin that were incubated overnight at 37° C. Eight colonies were randomly chosen to inoculate eight 5 ml overnight LB cultures in the presence of 12.5 µmol/ml ampicillin. Plasmids extracted from each liquid culture were analyzed by automated DNA sequencing using the fluorescence-based dideoxy chain termination reaction (Genewiz, North Brunswick, N.J.). It was found that they all contained the correct p53 17-26 cDNA reading frame associated with a stop codon and a start codon embedded in the Kozak sequence. This construct plasmid is termed p53 17-26-V ([expression] vector).

Precisely the same procedure was followed for preparation of a plasmid encoding a scrambled p53 peptide sequence (residues 12-26) as follows: 5'-AGTCGAATTCGCCACCA TGTGGGACCTGACACTACCCAAACAGCTTCTACCTT CAAGTTTGAATGAGCGGCCGCAGTC-3'(SEQ ID NO: 31), with start, stop codons, and restriction enzyme sites denoted as above. This plasmid construct is called p53-12-26-scrm-V Transfection into Cancer Cells.

Transfection of p53 17-26-V plasmid and the two control plasmids, one, the p53 12-26-scrm-V vector and the second vector encoding GFP only, called EV (empty vector) into MiaPaCa-2 and untransformed BMRPA1 cells was completed. These cells were evaluated for: viability and expression of: p53 protein, p53 17-26 peptide, caspase, annexin binding to phosphatidyl serine and LDH. Twenty four hours prior to transfection $5 \times 10^5$ cells were seeded in antibiotic-free medium into each well in a six-well tissue culture dish (TCD) and allowed to adhere overnight. To three wells, 0.8 ug of p53 17-26-V plasmid were added. To the other three wells, 0.8 ug of empty vector or p53-12-26-scrm-V vector encoding control peptide were added. To each of these wells, Lipofectamine 2000 transfection agent (Qiagen) was added such that the ratio of plasmid DNA (in ug) to Lipofectamine 2000 (in ul) was 1:2 (14). This ratio was determined in preliminary experiments described in the next paragraph. Transfections were performed in serum- and antibiotic-free culture medium at 37° C. for 4 h at which time the incubation was continued in complete medium, containing 10% fetal bovine serum (FBS) and penicillin and streptomycin (100 U/100 µg/ml). After another 4-5 h, the cells were washed followed by re-incubation in fresh complete medium. Transfection efficiency was measured by examining the frequency of GFP expressing cells in the total cell population 12 h post-transfection using a Zeiss LSM 410 Confocal Laser Scanning Microscope.

For each cell line the effective ratio of DNA:Lipofectamine 2000 reagent was studied and was verified in preliminary experiments using a checkerboard assay. In these experiments, transfection efficiency was established by titration of different concentrations of DNA in the presence of increasing concentrations of Lipofectamine 2000 on cells that had been seeded onto glass coverslips. After transfection the GFP-positive (GFP+) cells on the coverslips were quantitated by counting under a UV Light Zeiss Epifluorescence Microscope in 3-5 consecutive fields counting 200-400 cells. These preliminary experiments helped to establish the cell density, the amount of DNA and the DNA:Lipofectamine 2000 ratio to be used, and the time for transfection to proceed.

Expression of the p53 17-26 Peptide.

For protein analyses, and detection of apoptosis, $2 \times 10^6$ cells were seeded into 10 cm diameter TCDs and transfected with DNA: Lipofectamine 2000 proportionally adjusted to the increased area. When the cell density reached 90-100%, the cells of the experimental and sham-transfected group were detached using trypsin and plated into four new TCD's in which they were allowed to grow in complete medium. At defined time points cells were released from adherence with 10 mM EDTA in PBS and were lysed in lysing buffer [1% Triton X-100 in 0.05 M Tris-HCl (pH 8.0), 0.15 mM NaCl, 0.02% Na azide, 0.01 mg/ml phenylmethylsulfonylfluoride (PMSF), and 0.001 mg/ml Aprotinin]. Protein equivalents of $10^6$ cells, i.e., ~30 μg/lane, were then subjected to SDS-PAGE using 10% Tris-HCl gels and, in some experiments, 16% Tricine Peptide Gels (Biorad, Hercules, Calif.) to detect PNC-28 (~3104 Da) and p53 17-26 (~1500 Da). The separated proteins were then electrophoretically transferred to nitrocellulose membranes followed by immunoblotting with the mAb DO-1 to p53 AA residues 11-25, and with mAb B-2 to GFP (each at 1 μg-2.5 μg/ml blotting buffer), respectively (2). After washing non-reacted mAbs from the membranes, the membranes were incubated (1 h) with a second enzyme-labeled antibody from the ECL chemiluminescence kit (Amersham, Piscataway, N.J.) to detect the presence of p53 and p53 17-26 peptide. In preliminary experiments, it was noted that identification of p53 protein was easily possible within 30-90 sec of exposure while clear identifiable binding of mAbDO-1 to p53 17-26 peptide took much longer time. The membrane was therefore cut across the 17 kDa marker (kaleidoscope's polypeptide standard), to allow for the differential exposures. In addition, a time course of GFP expression was performed in both MiaPaCa-2 and BMRPA1 cells that established that, during the time period 48-96 h post-transfection, the cells showed the highest levels of GFP expression. Semi-quantitation of immunoblotting results was performed by measuring luminosity of bands in a single scanned developed x-ray film, using the histogram option of Adobe Photoshop 5.5. Background was ascertained by measuring average luminosity of 5 areas of the film outside the blotting region. Opacity of each band was calculated by the equation, Opacity=255-Luminosity-background (15).

Incubation of MiaPaCa-2 Cells with PNC-28.

Duplicate sets of $6 \times 10^6$ MiaPaCa-2 cells were incubated with different concentrations of PNC-28, i.e., 5, 10, 20, 40, 80 and 160 μmol/ml. Duplicate control experiments were also performed in which $6 \times 10^6$ MiaPaCa-2 cells were incubated with the control, PNC-29, present at a concentration of 75 mmol/ml. All incubations were carried out using a protocol identical to that described in ref. 1 (1). After the cells had been allowed to adhere to the tissue culture dish (TCD) for 24 hours the medium was removed from each TCD, and new medium containing the same or no peptide concentration was added. Medium from each TCD was removed every 24 h, and fresh medium with its respective peptide at the appropriate concentration was added. Cells were inspected daily for changes in cell growth, morphology, and viability. At the end of each day over a five-day period, duplicate cell counts were performed for each incubation using the trypan blue exclusion method. In addition, cell viability was also determined by 3-[4,5-dimethylthiazol-2-yl]-2,5 diphenyl tetrazolium bromide (MTT) assay according to the manufacturers' instructions (Promega Corporation, Madison, Wis., USA).

Incubation of Peptides with BMRPA1 Cells.

These cells are untransformed rat pancreatic acinar cells (1). Duplicate 5-day incubations were performed on $6 \times 10^6$ cells in three circumstances: with no peptide, with PNC-28 at 75 μmol/ml, and with PNC-29 at 75 μmol/ml. Cells were followed for viability and morphology over this time period. At the end of 5 days, cell counts were performed using the trypan blue exclusion method.

Immunocytochemistry for Annexin V-Binding to Phosphatidyl Serine.

To determine whether any of the transfected plasmids induced apoptosis, the cells were evaluated to determine whether the cells contained phosphatidyl serine in the inner cell membrane, identified as binding to annexin-V, as a marker for apoptosis (15). Cells ($5 \times 10^5$) were seeded in 6-well TCDs 24 h prior to transfection in antibiotic-free medium. Cells were then either transfected with p53 17-26-V, p53 12-26-scrm-V, EV or were left untreated. At predetermined time-points post-transfection, the cells were released using 0.5× Trypsin-EDTA, collected and processed as described in the manufacturer's instructions of the Annexin V-Biotin Apoptosis Detection Kit (CalBioChem, La Jolla, Calif.). The stained cells were resuspended in antifade (Molecular Probes, OR), mounted on glass slides under a glass coverslip and evaluated for red (TRITC) and green (GFP) fluorescence using confocal microscopy as described above.

Evaluation of Cells Treated with PNC-28 for Caspase as a Marker for Apoptosis and LDH Release as a Marker for Necrosis.

Cells from culture plates at 18, 44, 66 and 90 h time points were lysed in situ in cell lysis buffer [1% Triton X-100 in 0.05 M Tris-HCl (pH 8.0), 0.15 mM NaCl, 0.02% Na azide, 0.1 mg/ml phenylmethylsulfonylfluoride (PMSF), and 0.001 mg/ml Aprotinin]. Lysates were subjected to 10% SDS-PAGE followed by electrotransfer to nitrocellulose and immunoblotting with antibodies to GFP and p53 (Santa Cruz Biotechnology, Santa Cruz, Calif.). Antibody-labeled proteins were identified by chemiluminescence using ECL methodology (Amersham)(1). Assays for elevated caspase expression were performed using the Clontech (Palo Alto, Calif.) for caspase (CPP32) activity (2). As a positive control for the caspase activity assay, Mia-PaCa-2 cells were incubated with tumor necrosis factor (TNF) (Sigma, St. Louis, Mo.) at a concentration of 10 ng/ml for 24 h. In addition, to detect if significant cell necrosis occurred, the CytoTox96 assay was used (Promega, Madison, Wis.) for LDH released into the cell culture medium as performed on several breast cancer cell lines (2).

Electron Micropscopy of MiaPaCa-2 Cells Treated with PNC-28.

Time-lapse electron microscopy (EM) was used to examine the ultrastructural features of cell death. MiaPaCa-2 cells were grown for 24 h on Thermanox cover slips (Lux Scientific), and then treated with 25 μmol of PNC-28 for 1 and 15 min, along with a corresponding control group without peptide. The cells were washed with PBS solution and then fixed with 2.5% gluteraldehyde-PBS. The fixed cultures were rinsed in a 0.1 M phosphate buffer (pH 7.3), post fixed in 2% (0.08 m) osmium tetroxide-PBS (pH 7.3), dehydrated in a graded series of ethanol and propylene oxide and embedded in Epon 812. Sections were cut at 700 Å, stained with uranyl acetate and lead citrate and examined with a Jeol JEM 1010 Electron Microscope.

Blotting of Mia-PaCa-2 Cell Lysates for p53 and Waf$^{p21}$, a Target for Activated p53.

Cell lysates were prepared as described in the preceding paragraph and were subjected to immunoblotting with either DO-1 antibody described in the section above for expression of the p53 17-26 peptide, a (Ab-6) monoclonal anti-p53 antibody (Calbiochem,) or with polyclonal anti-waf$^{p21}$ antibody (Santa Cruz Biotechnology, Santa Cruz, Calif.) (1:2000 dilution) using a procedure identical to that described in the same section above. For controls, for actin was blotted for, using anti-actin polyclonal antibody (Santa Cruz Biotechnology).

Statistical Analysis.

Analysis of growth inhibition and markers for necrosis and apoptosis were analyzed by a two-tailed Mann-Whitney non-parametric test or a two-tailed Student T-test where appropriate. A P-value of less than 0.05 was considered significant.

Various changes and modifications can be made in the present invention. It is intended that all such changes and modifications come within the scope of the invention as set forth in the following claims.

What is claimed is:

1. A method of selectively necrosing cells, comprising:
providing a plurality of cells, including at least one cancer cell and at least one non-cancerous cell, wherein the at least one cancer cell has increased expression of HDM-2;
administering to the cells a compound, including a HDM-2 targeting component which is a peptide and a cytotoxic component which is a membrane resident peptide, said cytotoxic component attached to said HDM-2 targeting component at the carboxy terminus; wherein the compound binds to said at least one cancer cell and causes pore formation in a membrane thereof and wherein the compound is selected from the group consisting of PNC-27 and PNC-28; and
measuring in a cell medium contacted with the cells a level of LDH, whereby an increase in the level of LDH in the cell medium after administering the compound as compared to the level of LDH in the cell medium prior to administering the compound indicates necrosis of said at least one cancer cell.

2. The method of claim 1, further comprising the step of microscopy of the cells whereby membranolysis indicates necrosis of said at least one cancer cell.

3. The method of claim 1, further comprising the step of microscopy of the cells whereby morphology in the cells treated with the compound that is identical to untreated cells indicates the absence of necrosis.

4. A method of causing membranolysis in at least one cancer cell, comprising:
administering to at least one cancer cell, wherein the at least one cancer cell has increased expression of HDM-2, a compound comprising a HDM-2 targeting component which is a peptide and a pore-forming component which is a membrane resident peptide; whereby said pore-forming component is attached to said HDM-2 targeting component at the carboxy terminus and wherein the compound is selected from the group consisting of PNC-27 and PNC-28, wherein said administering step results in at least one transmembrane pore in a cancer cell membrane and
measuring in a cell medium contacted with said at least one cancer cell a level of LDH, whereby an increase in the level of LDH in the cell medium after administering the compound as compared to the level of LDH in the cell medium prior to administering the compound indicates necrosis of said at least one cancer cell.

5. The method of claim 4, wherein the said compound is administered at a dosage between 20 μmol/ml and 160 μmol/ml.

6. The method of claim 4, further comprising the step of microscopy of the cells using a light or electron microscope.

7. The method of claim 4, further comprising the step of microscopy of the cells whereby membranolysis indicates necrosis of said at least one cancer cell.

* * * * *

SEQUENCE LISTING

```
<160> NUMBER OF SEQ ID NOS: 32

<210> SEQ ID NO 1
<211> LENGTH: 17
<212> TYPE: PRT
<213> ORGANISM: Artificial sequence
<220> FEATURE:
<223> OTHER INFORMATION: Membrane resident peptide (MRP), reverseomer of
      Antennapedia

<400> SEQUENCE: 1

Lys Lys Trp Lys Met Arg Arg Asn Gln Phe Trp Val Lys Val Gln Arg
1               5                   10                  15

Gly

<210> SEQ ID NO 2
<211> LENGTH: 32
<212> TYPE: PRT
<213> ORGANISM: Artificial sequence
<220> FEATURE:
<223> OTHER INFORMATION: PNC-27

<400> SEQUENCE: 2

Pro Pro Leu Ser Gln Glu Thr Phe Ser Asp Leu Trp Lys Leu Leu Lys
1               5                   10                  15

Lys Trp Lys Met Arg Arg Asn Gln Phe Trp Val Lys Val Gln Arg Gly
                20                  25                  30

<210> SEQ ID NO 3
<211> LENGTH: 27
<212> TYPE: PRT
<213> ORGANISM: Artificial sequence
<220> FEATURE:
<223> OTHER INFORMATION: PNC-28

<400> SEQUENCE: 3

Glu Thr Phe Ser Asp Leu Trp Lys Leu Leu Lys Lys Trp Lys Met Arg
1               5                   10                  15

Arg Asn Gln Phe Trp Val Lys Val Gln Arg Gly
                20                  25

<210> SEQ ID NO 4
<211> LENGTH: 30
<212> TYPE: PRT
<213> ORGANISM: Artificial sequence
<220> FEATURE:
<223> OTHER INFORMATION: PNC-29

<400> SEQUENCE: 4

Met Pro Phe Ser Thr Gly Lys Arg Ile Met Leu Gly Glu Lys Lys Trp
1               5                   10                  15

Lys Met Arg Arg Asn Gln Phe Trp Val Lys Val Gln Arg Gly
                20                  25                  30
```

<210> SEQ ID NO 5
<211> LENGTH: 13
<212> TYPE: PRT
<213> ORGANISM: Artificial sequence
<220> FEATURE:
<223> OTHER INFORMATION: peptide from cytochrome P450 (aka "X13")

<400> SEQUENCE: 5

Met Pro Phe Ser Thr Gly Lys Arg Ile Met Leu Gly Glu
1               5                   10

<210> SEQ ID NO 6
<211> LENGTH: 30
<212> TYPE: PRT
<213> ORGANISM: Artificial sequence
<220> FEATURE:
<223> OTHER INFORMATION: PNC-7

<400> SEQUENCE: 6

Thr Ile Glu Asp Ser Tyr Arg Lys Gln Val Val Ile Asp Lys Lys Trp
1               5                   10                  15

Lys Met Arg Arg Asn Gln Phe Trp Val Lys Val Gln Arg Gly
            20                  25                  30

<210> SEQ ID NO 7
<211> LENGTH: 13
<212> TYPE: PRT
<213> ORGANISM: Artificial sequence
<220> FEATURE:
<223> OTHER INFORMATION: ras-p21 residues 35-47

<400> SEQUENCE: 7

Thr Ile Glu Asp Ser Tyr Arg Lys Gln Val Val Ile Asp
1               5                   10

<210> SEQ ID NO 8
<211> LENGTH: 15
<212> TYPE: PRT
<213> ORGANISM: Artificial sequence
<220> FEATURE:
<223> OTHER INFORMATION: PNC-26, residues 12-26 of the HDM-2 binding
      domain of p53

<400> SEQUENCE: 8

Pro Pro Leu Ser Gln Glu Thr Phe Ser Asp Leu Trp Lys Leu Leu
1               5                   10                  15

<210> SEQ ID NO 9
<211> LENGTH: 14
<212> TYPE: PRT
<213> ORGANISM: Artificial sequence
<220> FEATURE:
<223> OTHER INFORMATION: HIV-1 TAT(47-60), membrane resident peptide

<400> SEQUENCE: 9

Tyr Gly Arg Lys Lys Arg Arg Gln Arg Arg Arg Pro Pro Gln
1               5                   10

<210> SEQ ID NO 10
<211> LENGTH: 13
<212> TYPE: PRT
<213> ORGANISM: Artificial sequence
<220> FEATURE:
<223> OTHER INFORMATION: D-TAT, membrane resident peptide

<400> SEQUENCE: 10

```
Gly Arg Lys Lys Arg Arg Gln Arg Arg Pro Pro Gln
1               5                   10

<210> SEQ ID NO 11
<211> LENGTH: 13
<212> TYPE: PRT
<213> ORGANISM: Artificial sequence
<220> FEATURE:
<223> OTHER INFORMATION: R-TAT G(R)9PPQ, membrane resident peptide

<400> SEQUENCE: 11

Gly Ala Ala Ala Ala Ala Ala Ala Ala Pro Pro Gln
1               5                   10

<210> SEQ ID NO 12
<211> LENGTH: 7
<212> TYPE: PRT
<213> ORGANISM: Artificial sequence
<220> FEATURE:
<223> OTHER INFORMATION: SV40-NLS, membrane resident peptide

<400> SEQUENCE: 12

Pro Lys Lys Lys Arg Lys Val
1               5

<210> SEQ ID NO 13
<211> LENGTH: 16
<212> TYPE: PRT
<213> ORGANISM: Artificial sequence
<220> FEATURE:
<223> OTHER INFORMATION: nucleoplasmin-NLS, membrane resident peptide

<400> SEQUENCE: 13

Lys Arg Pro Ala Ala Ile Lys Lys Ala Gly Gln Ala Lys Lys Lys Lys
1               5                   10                  15

<210> SEQ ID NO 14
<211> LENGTH: 17
<212> TYPE: PRT
<213> ORGANISM: Artificial Sequence
<220> FEATURE:
<223> OTHER INFORMATION: HIV REV (34-50), membrane resident peptide

<400> SEQUENCE: 14

Thr Arg Gln Ala Arg Arg Asn Arg Arg Arg Trp Arg Glu Arg Gln
1               5                   10                  15

Arg

<210> SEQ ID NO 15
<211> LENGTH: 15
<212> TYPE: PRT
<213> ORGANISM: Artificial sequence
<220> FEATURE:
<223> OTHER INFORMATION: FHV (35-49) coat, membrane resident peptide

<400> SEQUENCE: 15

Arg Arg Arg Arg Asn Arg Thr Arg Arg Asn Arg Arg Arg Val Arg
1               5                   10                  15

<210> SEQ ID NO 16
<211> LENGTH: 19
<212> TYPE: PRT
<213> ORGANISM: Artificial sequence
<220> FEATURE:
<223> OTHER INFORMATION: BMV GAG (7-25), membrane resident peptide
```

<400> SEQUENCE: 16

Lys Met Thr Arg Ala Gln Arg Arg Ala Ala Arg Arg Asn Arg Trp
1               5                   10                  15
Thr Ala Arg

<210> SEQ ID NO 17
<211> LENGTH: 13
<212> TYPE: PRT
<213> ORGANISM: Artificial sequence
<220> FEATURE:
<223> OTHER INFORMATION: HTLV-II REX 4-16, membrane resident peptide

<400> SEQUENCE: 17

Thr Arg Arg Gln Arg Thr Arg Arg Ala Arg Arg Asn Arg
1               5                   10

<210> SEQ ID NO 18
<211> LENGTH: 19
<212> TYPE: PRT
<213> ORGANISM: Artificial sequence
<220> FEATURE:
<223> OTHER INFORMATION: CCMV GAG (7-25), membrane resident peptide

<400> SEQUENCE: 18

Lys Leu Thr Arg Ala Gln Arg Arg Ala Ala Ala Arg Lys Asn Lys Arg
1               5                   10                  15
Asn Thr Arg

<210> SEQ ID NO 19
<211> LENGTH: 17
<212> TYPE: PRT
<213> ORGANISM: Artificial sequence
<220> FEATURE:
<223> OTHER INFORMATION: P22 N (14-30), membrane resident peptide

<400> SEQUENCE: 19

Asn Ala Lys Thr Arg Arg His Glu Arg Arg Arg Lys Leu Ala Ile Glu
1               5                   10                  15
Arg

<210> SEQ ID NO 20
<211> LENGTH: 22
<212> TYPE: PRT
<213> ORGANISM: Artificial sequence
<220> FEATURE:
<223> OTHER INFORMATION: LAMBDA N(1-22), membrane resident peptide

<400> SEQUENCE: 20

Met Asp Ala Gln Thr Arg Arg Arg Glu Arg Arg Ala Glu Lys Gln Ala
1               5                   10                  15
Gln Trp Lys Ala Ala Asn
                20

<210> SEQ ID NO 21
<211> LENGTH: 18
<212> TYPE: PRT

```
<213> ORGANISM: Artificial sequence
<220> FEATURE:
<223> OTHER INFORMATION: Phi N (12-29), membrane resident peptide

<400> SEQUENCE: 21

Thr Ala Lys Thr Arg Tyr Lys Ala Arg Arg Ala Glu Leu Ile Ala Glu
1               5                   10                  15

Arg Arg

<210> SEQ ID NO 22
<211> LENGTH: 16
<212> TYPE: PRT
<213> ORGANISM: Artificial sequence
<220> FEATURE:
<223> OTHER INFORMATION: YEAST PRP6 (129-124), membrane resident peptide

<400> SEQUENCE: 22

Thr Arg Arg Asn Lys Arg Asn Arg Ile Gln Glu Gln Leu Asn Arg Lys
1               5                   10                  15

<210> SEQ ID NO 23
<211> LENGTH: 12
<212> TYPE: PRT
<213> ORGANISM: Artificial sequence
<220> FEATURE:
<223> OTHER INFORMATION: HUMAN U2AF, membrane resident peptide

<400> SEQUENCE: 23

Ser Gln Met Thr Arg Gln Ala Arg Arg Leu Tyr Val
1               5                   10

<210> SEQ ID NO 24
<211> LENGTH: 26
<212> TYPE: PRT
<213> ORGANISM: Artificial sequence
<220> FEATURE:
<223> OTHER INFORMATION: HUMAN C-FOS (139-164), membrane resident
      peptide

<400> SEQUENCE: 24

Lys Arg Arg Ile Arg Arg Glu Arg Asn Lys Met Ala Ala Ala Lys Ser
1               5                   10                  15

Arg Asn Arg Arg Arg Glu Leu Thr Asp Thr
            20                  25

<210> SEQ ID NO 25
<211> LENGTH: 28
<212> TYPE: PRT
<213> ORGANISM: Artificial sequence
<220> FEATURE:
<223> OTHER INFORMATION: HUMAN C-JUN (252-279), membrane resident
      peptide

<400> SEQUENCE: 25

Arg Ile Lys Ala Glu Arg Lys Arg Met Arg Asn Arg Ile Ala Ala Ser
1               5                   10                  15

Lys Ser Arg Lys Arg Lys Leu Glu Arg Ile Ala Arg
            20                  25

<210> SEQ ID NO 26
<211> LENGTH: 22
<212> TYPE: PRT
<213> ORGANISM: Artificial sequence
<220> FEATURE:
<223> OTHER INFORMATION: YEAST GCN4, membrane resident peptide
```

<400> SEQUENCE: 26

Lys Arg Ala Arg Asn Thr Glu Ala Ala Arg Ser Arg Ala Arg Lys
1               5                   10                  15

Leu Gln Arg Met Lys Gln
            20

<210> SEQ ID NO 27
<211> LENGTH: 18
<212> TYPE: PRT
<213> ORGANISM: Artificial sequence
<220> FEATURE:
<223> OTHER INFORMATION: Example membrane resident peptide (MRP)

<400> SEQUENCE: 27

Lys Leu Ala Leu Lys Leu Ala Leu Lys Ala Leu Lys Ala Ala Leu Lys
1               5                   10                  15

Leu Ala

<210> SEQ ID NO 28
<211> LENGTH: 18
<212> TYPE: PRT
<213> ORGANISM: Artificial sequence
<220> FEATURE:
<223> OTHER INFORMATION: p-vec, membrane resident peptide

<400> SEQUENCE: 28

Leu Leu Ile Ile Leu Arg Arg Arg Ile Arg Lys Gln Ala Lys Ala His
1               5                   10                  15

Ser Lys

<210> SEQ ID NO 29
<211> LENGTH: 8
<212> TYPE: PRT
<213> ORGANISM: Artificial sequence
<220> FEATURE:
<223> OTHER INFORMATION: (Arg)8 or any poly-R from (R)4-(R)16, membrane
      resident peptide

<400> SEQUENCE: 29

Arg Arg Arg Arg Arg Arg Arg Arg
1               5

<210> SEQ ID NO 30
<211> LENGTH: 10
<212> TYPE: DNA
<213> ORGANISM: Artificial sequence
<220> FEATURE:
<223> OTHER INFORMATION: Kozak sequence

<400> SEQUENCE: 30
gccaccatgg                                                            10

<210> SEQ ID NO 31
<211> LENGTH: 64
<212> TYPE: DNA
<213> ORGANISM: Artificial sequence
<220> FEATURE:
<223> OTHER INFORMATION: sense strand sequence of cDNA encoding the p53
      17-26 sequence

<400> SEQUENCE: 31
agtcgaattc gccaccatgg aaacattttc agacctatgg aaactacttt gagcggccgc    60
agtc                                                                  64

```
<210> SEQ ID NO 32
<211> LENGTH: 10
<212> TYPE: PRT
<213> ORGANISM: Artificial sequence
<220> FEATURE:
<223> OTHER INFORMATION: residues 17-26 of HDM-2 binding domain of p53

<400> SEQUENCE: 32

Glu Thr Phe Ser Asp Leu Trp Lys Leu Leu
1               5                   10
```